United States Patent
Miltenyi et al.

(10) Patent No.: US 7,166,423 B1
(45) Date of Patent: *Jan. 23, 2007

(54) DIRECT SELECTION OF CELLS BY SECRETION PRODUCT

(75) Inventors: Stefan Miltenyi, Bergisch Gladbach (DE); Andreas Radbruch, Bonn (DE); Rudi Manz, Köln-Sülz (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/416,920

(22) PCT Filed: Oct. 21, 1993

(86) PCT No.: PCT/US93/10126

§ 371 (c)(1),
(2), (4) Date: Apr. 21, 1995

(87) PCT Pub. No.: WO94/09117

PCT Pub. Date: Apr. 28, 1994

Related U.S. Application Data

(63) Continuation-in-part of application No. 07/965,934, filed on Oct. 21, 1992, now abandoned.

(51) Int. Cl.
*G01N 33/53* (2006.01)
*G01N 33/68* (2006.01)
*G01N 33/563* (2006.01)

(52) U.S. Cl. .......................... 435/2; 435/7.1; 435/7.2; 435/7.21; 435/7.5; 435/7.8; 435/7.9; 435/29; 435/961; 435/972; 435/975; 435/325; 436/501; 436/512; 436/536; 436/824; 424/93.7; 424/93.71

(58) Field of Classification Search ................. 435/2, 435/7.1, 7.2, 7.21, 7.5, 7.8, 7.9, 29, 235.1, 435/240.1, 240.2, 243, 961, 972, 975, 325; 436/501, 512, 536, 824; 530/350, 351, 387.1, 530/388.1, 387.3, 391.1, 391.3, 391.5, 402, 530/412, 413, 866; 424/93.7, 93.71
See application file for complete search history.

(56) References Cited

U.S. PATENT DOCUMENTS

| | | | |
|---|---|---|---|
| 4,281,061 A * | 7/1981 | Zuk et al. | |
| 4,557,979 A | 12/1985 | Higginbottom et al. | |
| 4,676,980 A * | 6/1987 | Segal et al. | ..................... 424/85 |
| 5,114,711 A * | 5/1992 | Bell et al. | .................. 424/85.1 |
| 6,576,428 B1 | 6/2003 | Assenmacher et al. | |

FOREIGN PATENT DOCUMENTS

| | | | |
|---|---|---|---|
| EP | 0186833 | | 7/1986 |
| EP | 0219309 | | 4/1987 |
| JP | 3-41087 | | 2/1991 |
| WO | WO 8906544 | * | 7/1989 |
| WO | WO 89/10758 | | 11/1989 |
| WO | WO 89/12110 | | 12/1989 |
| WO | WO 90/02334 | | 3/1990 |
| WO | WO 90/08197 | | 7/1990 |
| WO | WO 90/14435 | | 11/1990 |

OTHER PUBLICATIONS

Hunt, Chapter 55, from: "Handbook of Exp. Immunol., vol. 2, Cellular Imm.", Ed. D.M. Weir et al., Blackwell Sci, 1986, p. 55.1-55.18.*

Brennan et al., Science, 229:81-83, 1985.*

Barington et al., "An improved haemolytic plaque assay for the detection of cells secreting antibody to bacterial antigens" *J. Immunol. Met.* (1992) 146:129-137.

Barington et al., "A simplification of the enzyme-linked immunospot technique. Increased sensitivity for cells secreting IgG antibodies to *Haemophilus influenzae* type b capsular polysaccharide" *J. Immunol. Met.* (1992) 156:191-198.

Coco-Martin et al., "An isotype-specific spot-ELISA for the enumeration of antibody-secreting hybridomas and the determination of isotype switch variants" *J. Immunol. Met.* (1991) 145:11-18.

Of Conrad et al., "Immunoglobulin VH and VK genes of the BALB/c anti-foot-and-mouth disease virus (O1) VP1 response: cloning, characterization and transgenic mice" *Mol. Immunol.* (1991) 28:1201-1209.

Darveau et al., "Efficient preparation of human monoclonal antibody-secreting heterohybridomas using peripheral B lymphocytes cultured in the CD40 system" *J. Immunol. Met.* (1993) 159:139-143.

Eriksson et al., "Amplified ELISPOT assay for the detection of HIV-specific antibody-secreting cells in subhuman primates" *J. Immunol. Met.* (1992) 153:107-113.

Fischer et al., "Paucity of humoral response in patients to glioma-associated antigen(s): antigen localization by immunofluorescence" *Adv. Exp. Med. Biol.* (1991) 303:263-270.

Giordano et al., Repeated glucose stimulation reveals distinct and lasting secretion patterns of individual rat pancreatic B cells *J. Clin. Invest.* (1991) 87:2178-2185.

Isolauri et al., "Local immune response in patients with cow milk allergy: follow-up of patients retaining allergy or becoming tolerant" *J. Pediatr.* (1992) 120:9-15.

(Continued)

*Primary Examiner*—Ronald B. Schwadron
(74) *Attorney, Agent, or Firm*—Townsend and Townsend and Crew LLP

(57) ABSTRACT

Cells can be labeled with products which they secrete and release in an efficient manner by coupling the cells at their surface to a specific binding partner for the product and allowing the product to be captured by the specific binding partner as it is secreted and released. The product-labeled cells can then be further coupled to suitable labels, if desired, and separated according to the presence, absence, or amount of product.

289 Claims, 23 Drawing Sheets

OTHER PUBLICATIONS

Lalor et al., "Functional and molecular characterization of single, (4-hydroxy-3-nitrophenyl)acetyl (NP)-specific, IgG1+ B cells from antibody-secreting and memory B cell pathways in the C57BL/6 immune response to NP" *Eur. J. Immunol.* (1992) 22:3001-3011.

Of Liu et al., "Production of anti-tumor human monoclonal antibodies using different approaches" *Hum. Antibodies Hybridomas* (1993) 4:2-8.

Marder et al., "Selective cloning of hybridoma cells for enhanced immunoglobulin production using flow cytometric cell sorting and automated laser nephelometry" *Cytometry* (1990) 11:498-505.

Nesheim et al., "Diagnosis of human immunodeficiency virus infection by enzyme-linked immunospot assays in a prospectively followed cohort of infants of human immunodeficiency virus-seropositive women" *Pediatr. Infect. Dis. J.* (1992) 11:635-639.

Quiding et al., "Intestinal immune responses in humans. Oral cholera vaccination induces strong intestinal antibody responses and interferon-gamma production and evokes local immunological memory" *J. Clin. Invest.* (1991) 88:143-148.

Sakamoto et al., "Method for selecting anthocyanin-producing cells by a cell sorter" *Planta Med.* (1994) 60:253-259.

Shibata et al., "Clonal frequency analysis of B cells producing pathogenic anti-DNA antibody-associated idiotypes in systemic lupus erythematosus" *Clin. Immunol. Immunopathol.* (1992) 63:252-258.

Sparholt et al., "Detection of B-lymphocytes secreting antibodies to *Dermatophagoides* antigens" *Clin. Exp. Allergy* (1991) 21:85-90.

Steenbakkers et al., "A new approach to the generation of human or murine antibody producing hybridomas" *J. Immunol. Met.* (1992) 152:69-77.

Ufimtseva et al., "Mink-mouse interspecific hybridomas" *Hybridoma* (1991) 10:517-528.

Werner-Favre et al., "High IgE secretion capacity of human plasma cells" *Eur. J. Immunol.* (1993) 23:2038-2040.

Köhler et al., "Immunoglobulin M Mutants" *Eur. J. Immunol.* (1980) 10:467-476.

Nir et al., "Single-Cell Entrapment and Microcolony Development within Uniform Microspheres Amendable to Flow Cytometry", *Applied and Environ. Microbiol.* (1990) 56(9):2870-2875.

Nir et al., "Flow Cytometry Sorting of Viable Bacteria and Yeasts According to β-Galactosidase Activity", *Applied and Environ. Microbiol.* (1991) 56(12):3861-3866.

Ehrlich et al., "Marker and Function Analysis of Natural Killer and Alloreactive T Cells during Early Stages of Dimethylbenzanthracene Carcinogenesis", *Nat. Immun. Cell Growth Regul.* (1986) 5:305-316.

Greenstein et al., "Flow Sorting of Antigen-binding B Cell Subsets", *J. Immunol.* (1980) 124(3):1472-1481.

Greenstein et al., "Functional Subsets of B Cells defined by Quantitative differences in Surface /-A", *J. Immunol.* (1981) 126:2419-2423.

Kleinberger et al., "Carcinogen-mediated co-activation of two independent genes in Chinese hamster cells", *Carcinogenesis* (1988) 9(6):979-985.

Letwin et al., "An Improved Clonal Excess Assay Using Flow Cytometry and B-Cell Gating", *Blood* (1990) 75(5):1178-1185.

Marti et al., "Normal Human Blood Density Gradient Lymphocyte Subset Analysis", *Amer. J. Hematol.* (1985) 20:41-52.

Michalevicz et al., (1989) "Characterization of Lympho-Myeloid-Erythroid-Megakaryocytic Stem Cells in Peripheral Blood of Hairy Cell Leukemia Patients", *Leukemia Res.* 13(10):915-920.

Slezak et al., "Fluorescent in Vivo Tracking of Hematopoietic Cells. Part I. Technical Considerations", *Blood* (1989) 74(6):2172-2177.

Slezak et al., "Cell-mediated Cytotoxicity" A Highly Sensitive and Informative Flow Cytometric Assay, *J. Immunol. Meth.* (1989) 117:205-214.

Koga et al., "Synthesis and release of interleukin 1 by reoxygenated human mononuclear phagocytes" *J. Clin. Invest.* (1992) 90:1007-1015.

Parks et al., "Antigen-specific identification and cloning of hybridomas with a fluorescence-activated cell sorter" *Proc. Natl Acad. Sci. USA* (1979) 76:1962-1966.

Weissman et al.,"Only high-affinity receptors for interleukin 2 mediate internalization of ligand" *Proc. Natl. Acad. Sci. USA* (1986) 83:1463-1466.

Deniz et al., "Human NK1 and NK2 subsets determined by purification of IFN-γ-secreting and IFN-γ-nonsecreting NK cells," *Eur. J. Immunol.*, 32:879-884 (2002).

Edwards et al., "Microbial Recopgnition Via Toll-Like Receptor-Dependent and -Independent Pathways Determines the Cytokine Response of Murine Dendritic Cell Subsets to CD40 Triggering," *J. Immunology*, 169:3652-3660 (2002).

Hayakawa et al., "Critical contribution of IFN-γ-and NK cells, but not perforin-mediated cytotoxicity, to anti-metastatic effect of a αgalactosylceramide," *Eur. J. Immunol.*, 31:1720-1727 (2001).

Hu-Li et al., "Regulation of Expression of *IL-4* Alleles: Analysis Using a Chimeric *GFP/IL-4* Gene," *Immunity*, 14:1-11 (2001).

Yang et al., "Immunoregulatory Role of CD1d in the Hydrocarbon Oil-Induced Model of Lupus Nephritis," *J. Immunology*, 171:2142-2153 (2003).

Manz et al., "Analysis and sorting of live cells according to secreted molecules, relocated to a cell-surface affinity matrix" *Proc. Natl. Acad. Sci. USA* (1995) 92:1921-1925.

\* cited by examiner

NO STAIN

ST - FITC

ST - FITC

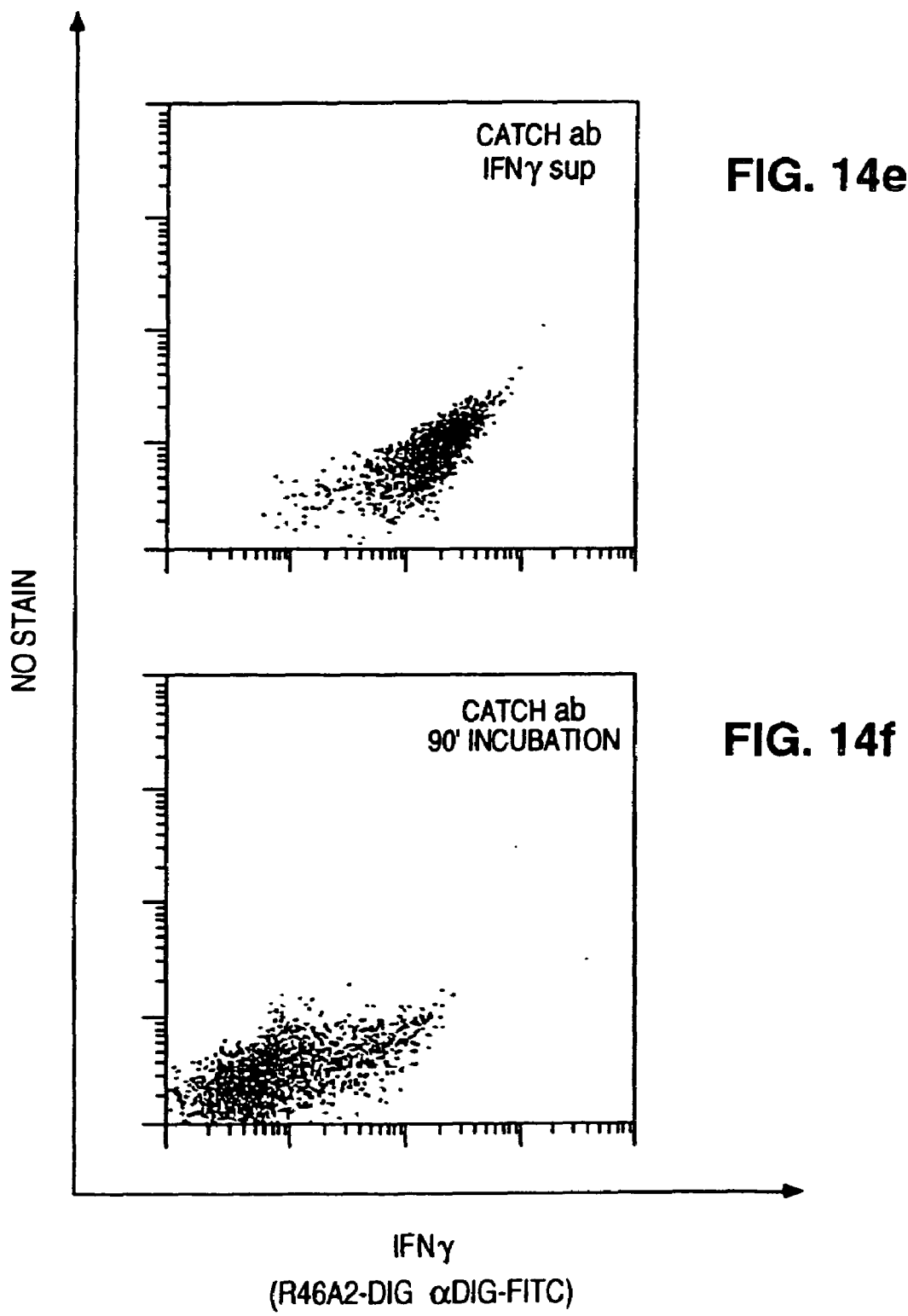

DIRECT SELECTION OF CELLS BY SECRETION PRODUCT

This application is a continuation-in-part of U.S. patent application Ser. No. 07/965,934, filed Oct. 21, 1992, now abandoned.

TECHNICAL FIELD

The invention is in the field of analysis of cell populations and cell separation. More particularly, the invention concerns analysis and separation techniques based on primary labeling of cells with their secreted products through capture of these products by a specific binding partner for the product anchored to the cell surface.

BACKGROUND ART

Numerous attempts have been made to analyze populations of cells and to separate cells based on the products which they produce. Such approaches to cell analysis and separation are especially useful in assessing those cells which are capable of secreting a desired product (the "product"), or which are relatively high secretors of the product. These methods include cloning in microtiter plates and analysis of the culture supernatant for product, cloning in agar and analysis by methods for identification of the product of the localized cells; the identification methods include, for example, plaque assays and western blotting. Most methods for analysis and selection of cells based upon product secretion use the concept of physical isolation of the cell, followed by incubation under conditions that allow product secretion, and screening of the cell locations to detect the cell or cell clones that produce the product. For cells in suspension, after the cells have secreted the product, the product diffuses from the cell without leaving a marker to allow identification of the cell from which it was secreted. Thus, secretor cells cannot be separated from non-secretor cells with this system.

In other cases, both secretor and non-secretor cells may associate the product with the cell membrane. An example of this type of system are B-cell derived cell lines producing monoclonal antibodies. It has been reported that these types of cell lines were separated by fluorescence activated cell sorting (FACS) and other methods reliant upon the presence of antibody cell surface markers. However, procedures that analyze and separate cells by markers that are naturally associated with the cell surface may not accurately identify and/or be used in the separation of secretor cells from non-secretor cells. In addition, systems such as these are not useful in identifying quantitative differences in secretor cells (i.e., low level secretors from high level secretors).

A method that has been used to overcome the problems associated with product diffusion from the cells has been to place the cell in a medium that inhibits the rate of diffusion from the cell. A typical method has been to immobilize the cell in a gel-like medium (agar), and then to screen the agar plates for product production using a system reliant upon blotting, for example western blots. These systems are cumbersome and expensive if large numbers of cells are to be analyzed for properties of secretion, non-secretion, or amount of secretion.

Kohler et al. have described a system in which mutants of a hybridoma line secreting IgM with anti-trinitrophenyl (anti-TNP) specificity were enriched by coupling the hapten to the cell surface and incubating the cells in the presence of complement. In this way, cells secreting wild-type Ig committed suicide, whereas cells secreting IgM with reduced lytic activity or not binding to TNP preferentially survived. Kohler and Schulman, Eur. J. Immunol. 10:467–476 (1980).

Other known systems allow the cells to secrete their products in the context of microdroplets of agarose gel which contain beads that bind the products, and encapsulation of the cells. Such methods have been disclosed in publications by Nir et al., Applied and Environ. Microbiol. 56:2870–2875 (1990); and Nir et al., Applied and Environ. Microbial. 56:3861–3866 (1990). These methods are unsatisfactory for a variety of reasons.

In the process of microencapsulation, statistical trapping of numbers of cells in the capsules occurs, resulting in either a high number of empty capsules when encapsulation occurs at low cell concentrations, or multiple cells per capsule when encapsulation occurs at high cell concentrations. In order to analyze and separate single cells or single cell clusters by this technique, large volumes must be handled to work with relatively small numbers of cells because of the numbers of empty capsules and because of the size of the microcapsules (50–100 µm). The large volume of droplets results in background problems using flow cytometry analysis and separation. In addition, the capsules do not allow separation using magnetic beads or panning for cell separation.

Various methods have been used to couple labels to cell surfaces where the label is intended for direct detection, such as a fluorochrome. For example, the use of hydrophobic linkers inserted into the cell membrane to couple fluorescent labels to cells have been described in PCT WO 90/02334, published 8 Mar. 1990. Antibodies directed to HLA have also been used to bind labels to cell surfaces. Such binding results in a smaller dimension than the encapsulated droplets described above and such cells can conveniently be used in standard separation procedures including flow cytometry and magnetic separations.

It has now been found that by anchoring a specific binding partner into the cell surface using an appropriate coupling mechanism, products of the cells can be captured and cells sorted on the basis of the presence, absence or amount of product.

DISCLOSURE OF THE INVENTION

The invention provides a method for convenient analysis and cell separation based on the products secreted by the cells. The cells are provided with a capture moiety for the product, which can then be used directly as a label. The binding of the product to the capture moiety results in a "captured product." Alternatively, the cells are bound to the product via the capture moiety and can be further labeled via label moieties which bind specifically to the product and that are, in turn, labeled either directly or indirectly with traditional labeling materials such as fluorophores, radioactive isotopes, chromophores or magnetic particles.

The labeled cells may then be separated or detected using standard cell sorting techniques based on these labels. Such techniques include flow cytometry, magnetic separation, high gradient magnetic separation, centrifugation, and the like.

Thus, in one aspect, the invention encompasses a method to separate cells according to a product secreted and released by the cells, which method comprises effecting a separation of cells according to the degree to which they are labeled with said product, wherein labeling with the product is achieved by coupling the surface of the cells to at least one capture moiety; culturing the cells under conditions wherein the product is secreted, released and specifically bound ("captured" or "entrapped") to said capture moiety; and labeling the captured product with the label moiety; wherein the labeled cells are not lysed as part of the separation procedure.

Another aspect of the invention is a composition of matter which comprises cells capable of capturing a product secreted and released by the cells wherein the surface of the cells is coupled to a capture moiety. Still another aspect of the invention is cells and progeny thereof separated by the above-described method.

Yet another aspect of the invention is a method to label cells with a product secreted and released by the cells, which method comprises coupling the surface of the cells to a capture moiety, and culturing the cells under conditions wherein the product is secreted and released. The captured product may be separately labeled by a label moiety.

An additional aspect of the invention is a method of analyzing a population of cells to determine the proportion of cells that secrete a varying amount of product relative to other cells in the population, the method comprising labeling the cells by the above-described method, further labeling the cells with a second label that does not label the captured product, and detecting the amount of product label relative to the second cell label.

Another additional aspect of the invention is a method of determining a distribution of secretory activity in a population of cells, the method comprising labeling cells by the method described above (i.e. coupling the surface of said cells to a capture moiety, culturing the cells under conditions wherein the product is secreted and released and exposing the cells to a label moiety) and determining the amount of product per cell by the amount of label moiety bound to the cell.

Yet another additional aspect of the invention is a method of determining a distribution of secreted products and secretory activity for each secreted product in a population of cells, the method comprising labeling cells by the method described above by coupling the surfaces of cells in the population with capture moieties for each secreted product to be detected; culturing the cells under conditions wherein the products are secreted and released, labeling the secreted captured products, with label moieties, wherein the label moiety for each secreted capture product is distinguishable; and determining the amount and type of product per cell.

Still another aspect of the invention is a kit for use in the detection of cells that secrete a desired product. The kit may contain a physiologically acceptable medium which may be of varying degrees of viscosity up to a gel-like consistency, said medium to be used for cell incubation for the production of the secreted product; a product capture system comprised of at least one anchor moiety and at least one capture moiety; at least one label moiety; and instructions for use of the reagents, all packaged in appropriate containers.

Another aspect of the invention is a kit for use in the detection and/or separation of cells that secrete a desired product. The kit contains at least one capture moiety which is a bifunctional antibody with specificity for both the cells and the product and at least one label moiety. These reagents may, preferably, be placed in a single vial for simultaneous capture and labeling. Instructions for use of reagents should also be included. A physiologically acceptable medium of varying viscosities or gel forming abilities may also be provided. The liquid phase may however be provided by the sample itself including but not limited to cell culture medium, blood and urine.

BRIEF DESCRIPTION OF THE DRAWINGS

FIG. 7 are photocopies of traces of FACScan showing the effect of the concentration of methylcellulose in the medium on capture.

FIGS. 9a, 9b, and 9c show the capture of product by anti-product antibodies on cells when the cells are incubated in culture medium, culture medium with 40% bovine serum albumin (BSA), and culture medium with 20% BSA plus 20% gelatin, respectively.

MODES OF CARRYING OUT THE INVENTION

Figure 1:
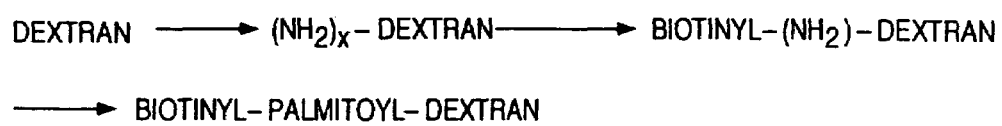
FIG. 1 is a scheme for the introduction of biotinyl and palmitoyl groups onto Dextran.

The invention employs a mechanism for the capture of products secreted from cells. The method permits products secreted by eukaryotic and prokaryotic cells or cell aggregates to be captured at the surface of the cell. The captured product permits the cell to be detected, analyzed, and if desired, sorted according to the presence, absence, or amount of the product present. The means of capture comprise a capture moiety which has been anchored to the cell surface by a means suitable for the cell to be sorted. As used herein, the term "cell" or "cells" include cell aggregates; cell aggregates are groups of cells that produce a designated secreted product and are known in the art, and include, for example, the islets of Langerhans. As used herein products which can be identified include any products secreted by the cells. Such products include, but are not limited to, cytokines like IFNγ, IL1, IL2, IL4, IL10, IL12, TGFβ, TNF, GMCSF, and SCF, antibodies, hormones, enzymes and proteins.

The capture moiety may be coupled to the anchoring means (the "anchor moiety") optionally through a linking moiety, and may also include a linking moiety which multiplies the number of capture moieties available and thus the potential for capture of product, such as branched polymers, including, for example, modified dextran molecules, polyethylene glycol, polypropylene glycol, polyvinyl alcohol, and polyvinylpyrrolidone.

For cells without cell walls, such as mammalian or other animal cells or cell protoplasts, suitable anchor moieties to the cell surface include lipophilic molecules such as fatty acids. Examples of suitable cell surface molecules include, but are not limited to, any molecule associated with the cell surface. Suitable molecules include, but are not limited to, cell surface markers such as CD45 (pan leukocyte), anti-β2 microglobulin, CD3 (T cells (activating)), CD4, CD8, and other CD markers or cell adhesion molecules. Alternatively, antibodies or other agents which specifically bind to cell surface molecules such as the MHC antigens or glycoproteins, could also be used. For cells which have cell walls, such as plant cells, fungi, yeast or bacteria, suitable anchor moieties include binding agents to cell wall components, including, for example, antibodies or lectins.

Specific binding partners include capture moieties and label moieties. The capture moieties are those which attach both to the cell, either directly or indirectly, and the product. The label moieties are those which attach to the product and may be directly or indirectly labeled. Specific binding partners include any moiety for which there is a relatively high affinity and specificity between product and its binding partner, and in which the dissociation of the product:partner complex is relatively slow so that the product:partner complex is detected during the labeling or cell separation technique.

Specific binding partners may include, but are not limited to, substrates or substrate analogs to which a product will bind. These substrates include, but are not limited to, peptides, polysaccharides, steroids, biotin, digitoxin, digitonin, and other molecules able to bind the secreted product, and in a preferred embodiment will include antibodies. When the capture moiety is an antibody it may be referred to as the "capture antibody" or "catch antibody." As used herein, the term "antibody" is intended to include polyclonal and monoclonal antibodies, chimeric antibodies, haptens and antibody fragments, bispecific antibodies and molecules which are antibody equivalents in that they specifically bind to an epitope on the product antigen.

Bispecific antibodies, also known as bifunctional antibodies, have at least one antigen recognition site for a first antigen and at least one antigen recognition site for a second antigen. Such antibodies can be produced by recombinant DNA methods or chemically by methods known in the art. Chemically created bispecific antibodies include but are not limited to antibodies that have been reduced and reformed so as to retain their bivalent characteristics and antibodies that have been chemically coupled so that they have at least two antigen recognition sites for each antigen. Bispecific antibodies include all antibodies or conjugates of antibodies, or polymeric forms of antibodies which are capable of recognizing two different antigens. Antibodies can be immobilized on a polymer or particle.

In the practice of the invention, the capture moiety can be attached to a cell membrane (or cell wall) by a variety of methods. Suitable methods include, but are not limited to, direct chemical coupling to amino groups of the protein components; coupling to thiols (formed after reduction of disulfide bridges) of the protein components; indirect coupling through antibodies (including pairs of antibodies) or lectins; anchoring in the lipid bilayer by means of a hydrophobic anchor moiety; and binding to the negatively charged cell surface by polycations.

In other embodiments of the invention, the capture moiety is introduced using two or more steps, e.g., by labeling the cells with at least one anchor moiety which allows the coupling of the capture moiety to the anchor moiety either directly for instance by a biotin/avidin complex or indirectly through a suitable linking moiety or moieties.

Methods for direct chemical coupling of antibodies to the cell surface are known in the art, and include, for example, coupling using glutaraldehyde or maleimide activated antibodies. Methods for chemical coupling using multiple step procedures include, for example, biotinylation, coupling of TNP or digoxigenin using, for example, succinimide esters of these compounds. Biotinylation may be accomplished by, for example, the use of D-biotinyl-N-hydroxysuccinimide. Succinimide groups react effectively with amino groups at pH values above 7, and preferentially between about pH 8.0 and about pH 8.5. Biotinylation may also be accomplished by, for example, treating the cells with dithiothreitol (DTT) followed by the addition of biotin maleimide.

Coupling to the cells may also be accomplished using antibodies against cell surface antigens ("markers"). Antibodies generally directed to surface antigens may be required in the range of about 0.1 to 1 µg of antibody per $10^7$ cells, however, this requirement will vary widely in response to the affinity of the antibody to the product and will need to be determined empirically. Such a determination is well within the skill of one in the art. Thus, the appropriate amount of antibody must be determined empirically and is within the skill of one in the art. This allows coupling to specific cells based on cell type specific marker expression. For instance, classes of cells such as T cells or subsets thereof can be specifically labeled. As a capture moiety, a bispecific antibody may be used which has an antigen recognition site for the cell or an anchor moiety placed thereon, and for the product.

A capture moiety, particularly capture antibodies should be selected based on the amount of secreted product. For example, for cells which secrete only a few molecules, a high affinity antibody should be chosen so as to catch most of the secreted molecules. Alternatively, in the case where the cell secretes many molecules during the incubation time, a lower affinity antibody may be preferred to prevent too early saturation of the catching matrix. Determination of suitable affinities for the level of proteins secreted are determined empirically and are within the skill of one in the art.

Cells carrying large amounts of N-acetylneuraminic acid on their surface as a constituent of their lipopolysaccharides bear a negative charge at physiological pH values. Coupling of capture moieties may be via charge interactions. For example, capture moieties bearing polycations bind to negatively charged cells. Polycations are known in the art and include, for example, polylysine and chitosan. Chitosan is a polymer consisting of D-glucosamine groups linked together by β-(1–4) glucoside bonds.

Another method of coupling capture moieties to the cells is via coupling to the cell surface polysaccharides. Substances which bind to polysaccharides are known in the art, and include, for example, lectins, including concanavalin A, *solanum tuberosum, aleuria aurantia, datura stramonium, galanthus nivalis, helix pomatia, lens culinaris* and other known lectins supplied by a number of companies including for example, Sigma Chemical Company and Aldrich Chemical Company.

In some embodiments of the invention, the capture moiety is coupled to the cell by hydrophobic anchor moieties to the cell membrane. Suitable hydrophobic anchor moieties that will interact with the lipid bilayer of the membrane are known in the art, and include, but are not limited to, fatty acids and non-ionic detergents (including, e.g., TWEEN-80™. A drawback to attachment of the capture moiety to the cell via the insertion of an anchor moiety is that the rate of integration of the anchor moiety into the cell is low. Thus, high concentrations of the anchor moiety often are required. This latter situation is often uneconomical when the capture moiety is a relatively limited or expensive substance, for example, an antibody.

The low yield of hydrophobic anchor moieties that embed themselves in the membrane is relevant only when these molecules are available in relatively limited quantities. This problem may be overcome by using a bridging system that includes an anchor moiety and a capture moiety, wherein one of the moieties is of higher availability, and wherein the two parts of the bridging system have a high degree of specificity and affinity for each other. For example, in one embodiment, avidin or streptavidin is attached to the cell surface via a hydrophobic anchor moiety, while the capture moiety is a biotinylated anti-product antibody. In another embodiment, the cell surface is labeled with digoxigenin followed by bispecific antibodies having specificity for both digoxigenin and the product. This approach can be used with other pairs of molecules able to form a link, including, for example, hapten with antihapten antibodies, NTA with polyhistidine residues, or lectins with polysaccharides. A preferred embodiment is one which allows "amplification" of the system by increasing the number of capture moieties per anchor moiety.

In one illustrative embodiment, a branched dextran is bound to palmitic acid, thus providing a multiplicity of available binding sites. The dextran is in turn coupled to biotin and treated with avidin-conjugated antibody specific for the product.

It is of course contemplated within the embodiments of the invention that linker moieties may be used between the anchor moiety and the capture moiety when the anchor moiety is coupled in any fashion to the cell surface. Thus, for example, an avidin (or streptavidin) biotin linker moiety may link an antibody anchor moiety with a capture moiety. Bispecific antibody systems may also act as linker moieties.

In order to analyze and, if desired, to select cells that have the capability of secreting the product of interest, cells modified as above to contain the capture moiety are incubated under conditions that allow the production and secretion of the product in a sufficient amount to allow binding to and detection of the cells that contain the captured product. These conditions are known to those of skill in the art and include, inter alia, appropriate temperature, pH, and concentrations of salts, growth factors and substrates in the incubation medium, as well as the appropriate concentrations of gas in the gaseous phase. When it is desirable to distinguish between high and low producer cells, the time of incubation is such that product secretion by the cells is still in a linear phase. The appropriate conditions can be determined empirically and such a determination is within the skill of one in the art. Additionally, secretion by the cells can be modified, that is upregulated, induced, or reduced using a biological modifier. Suitable biological modifiers include, but are not limited to, molecules and other cells. Suitable molecules include, but are not limited to, drugs, cytokines, small molecules, hormones, combinations of interleukins, lectins and other stimulating agents e.g. PMA, LPS, bispecific antibodies and other agents which modify cellular functions or protein expression.

Other ways of modifying secretion by cells include, but are not limited to, direct cell to cell interactions such as between a tumor and T cell and indirect cell to cell interactions such as those induced by the proximity of other cells which secrete a biological modifier. Suitable cells include, but are not limited to, blood cells, peripheral bone marrow cells (PBMC) and various cell lines. The biological modifiers can be added at any time but are preferably added to the incubation medium. Alternatively, the cells can be pretreated with these agents or cells prior to the incubation step.

The incubation conditions are also such that product secreted by a producer cell is essentially not captured by another cell, so distinguishing non-producing cells from product producing cells, or high producers from low producers is possible. Generally the incubation time is between 5 minutes and ten hours, and more usually is between 1 and 5 hours. The incubation medium may optionally include a substance which slows diffusion of the secreted product from the producer cell. Substances which inhibit product diffusion in liquid media and that are non-toxic to cells are known in the art, and include, for example, a variety of substances that partially or completely gel, including, for example, alginate, low melting agarose and gelatin. By varying the viscosity or permeability of the medium, the local capture by a producing cell of certain sizes of secreted products can be modulated. The molecular weight size exclusion of the medium can be adjusted to optimize the reaction. The optimal composition of the medium can be empirically determined and is influenced by the cell concentration, the level of secretion and molecular weight of the product and the affinity of the capture antibodies for the product. Such a determination is within the skill of one in the art.

Preferably, the gels are solubilized after the incubation to allow for the isolation of the cells or groups of cells from the media by cell sorting techniques. Thus, for example, the gels may be linked by disulfide bonds that can be dissociated by sulfhydryl reducing agents such as β-mercaptoethanol or DTT or the gels may contain ionic cross-linkings, including for example, calcium ions, that are solubilized by the addition of a chelating agent such as EDTA.

In a preferred embodiment, during the secretion phase, the cells are incubated in a gelatinous medium, and preferentially the size limitation of penetration into the gel prevents the product from substantially entering the gel.

An alternative or addition to using a viscous or gelatinous medium to prevent unspecific cell cross-contamination is to provide a capture system for capturing products not captured by the cell surface capture system on the secreting cell. For example, this technique can be used in the case where many cell types produce a product or dead cells unspecifically release large amounts of unwanted products or if no sufficient diffusion barrier can be created between the cells. This can be accomplished by adding to the medium surrounding the cells beads (e.g. latex beads) conjugated to an antibody product from the supernatant. Alternatively, gels with immobilized antibodies or other moieties being able to remove unbound product from the medium might be employed. These trapping moieties are capable of retaining these unwanted products or preventing them from binding to the nonsecreting cells by binding to the non-retained products. This "junk capture system" might be immobilized into the gel matrix or it may be attached to magnetic or other types of particles. The location and catching characteristics of the junk capture system should be adjusted so that sufficient product molecules are specifically bound to the secreting cells thus minimizing background on non-producing cells.

At the end of the secretion phase the cells are usually chilled to prevent further secretion, and the gel matrix (if any) is solubilized. This order may, of course, be reversed. The cells containing the captured product are then labeled with a label moiety. Labeling may be accomplished by any method known to those of skill in the art. For example, anti-product antibodies may be used to directly or indirectly label the cells containing the product. The labels used are those which are suitable for use in systems in which cells are to be analyzed or sorted based upon the attachment of the label moiety to the product.

In other embodiments, capture moieties that do not contain captured product may be detected. This allows, for example, the isolation of cells that secrete high amounts of product by employing a negative separation method, i.e., detection of cells not highly saturated with product. The cells can be labeled with other substances recognizing, including, but not limited to, cell surface markers, cell type, cellular parameters such as DNA content, cell status, or number of capture moieties.

The enumeration of actual capture moieties can be important to compensate for varying amounts of these molecules due to, for example, different conjugation potentials of the cells. It may be especially important for the isolation of rare cells to exclude cells with decreased or increased capability for binding the product capture system, including the anchor and capture moieties.

Analysis of the cell population and cell sorting based upon the presence of the label may be accomplished by a number of techniques known in the art. Cells can be analyzed or sorted by, for example, flow cytometry or FACS. These techniques allow the analysis and sorting according to one or more parameters of the cells. Usually one or multiple secretion parameters can be analyzed simultaneously in combination with other measurable parameters of the cell, including, but not limited to, cell type, cell surface antigens, DNA content, etc. The data can be analyzed and cells can be sorted using any formula or combination of the measured parameters. Cell sorting and cell analysis methods are known in the art and are described in, for example, THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 1992). Cells can also be analyzed using microscopy techniques including, for example, laser scanning microscopy, fluorescence microscopy; techniques such as these may also be used in combination with image analysis systems. Other methods for cell sorting include, for example, panning and separation using affinity techniques, including those techniques using solid supports such as plates, beads and columns.

Some methods for cell sorting utilize magnetic separations, and some of these methods utilize magnetic beads. Different magnetic beads are available from a number of sources, including for example, Dynal (Norway), Advanced Magnetics (Cambridge, Mass., U.S.A.), Immuncon (Philadelphia, U.S.A.), Immunotec (Marseille, France), and Miltenyi Biotec GmbH (Germany).

Preferred magnetic labeling methods include colloidal superparamagnetic particles in a size range of 5 to 200 nm, preferably in a size of 10 to 100 nm. These magnetic particles allow a quantitative magnetic labeling of cells, thus the amount of coupled magnetic label is proportional to the amount of bound product, and the magnetic separation methods are sensitive to different amounts of product secretion. Colloidal particles with various specificities are known in the art, and are available, for example, through Miltenyi Biotec GmbH. The use of immunospecific fluorescent or magnetic liposomes may also be used for quantitative labeling of captured product. In these cases, the liposomes contain magnetic material and/or fluorescent dyes conjugated with antibody on their surfaces, and magnetic separation is used to allow optimal separation between nonproducing, low producing, and high producing cells.

The magnetic separation can be accomplished with high efficiency by combining a second force to the attractive magnetic force, causing a separation based upon the different strengths of the two opposed forces. Typical opposed forces are, for example, forces induced by magnetic fluids mixed in the separation medium in the magnetic separation chamber, gravity, and viscous forces induced by flow speed of medium relative to the cell. Any magnetic separation method, preferably magnetic separation methods allows quantitative separation, can be used. It is also contemplated that different separation methods can be combined, for example, magnetic cell sorting can be combined with FACS, to increase the separation quality or to allow sorting by multiple parameters.

Preferred techniques include high gradient magnetic separation (HGMS), a procedure for selectively retaining magnetic materials in a chamber or column disposed in a magnetic field. In one application of this technique the product is labeled by attaching it to a magnetic particle. The attachment is generally through association of the product with a label moiety which is conjugated to a coating on the magnetic particle which provides a functional group for the conjugation. The product associated with the cell and coupled to a magnetic label is suspended in a fluid which is then applied to the chamber. In the presence of a magnetic gradient supplied across the chamber, the magnetically labeled cell is retained in the chamber; if the chamber contains a matrix, it becomes associated with the matrix. Cells which do not have or have only a low amount of magnetic labels pass through the chamber.

The retained cells can then be eluted by changing the strength of, or by eliminating, the magnetic field or by introducing a magnetic fluid. The selectivity for a captured product is supplied by the label moiety conjugated either directly or indirectly to the magnetic particle or by using a primary antibody and a magnetic particle recognizing the primary antibody. The chamber across which the magnetic field is applied is often provided with a matrix of a material of suitable magnetic susceptibility to induce a high magnetic field gradient locally in the chamber in volumes close to the surface of the matrix. This permits the retention of fairly weakly magnetized particles. Publications describing a variety of HGMS systems are known in the art, and include, for example, U.S. Pat. No. 4,452,773, U.S. Pat. No. 4,230,685, PCT application WO 85/04330, U.S. Pat. No. 4,770,183, and PCT/EP89/01602; systems are also described in U.S. Ser. No. 07/291,177 now abandoned and in U.S. Ser. No. 07/291,176 now abandoned, which are commonly owned and hereby incorporated herein by reference.

As seen from above, processes embodied by the invention include the following steps:

a. Coupling an anchor moiety to the surface of the cells suspected of secreting a product;

b. coupling to the anchor moiety a capture moiety which captures secreted product;

c. incubating the cells with the coupled capture moiety to allow synthesis and secretion of the product under conditions whereby the product binds to the capture moiety; and d. labeling the captured product with a label moiety.

In addition, in other embodiments, the processes include labeling the cells that contain captured product, if any. Other embodiments may also include analyzing the cell population to detect labeled cells, if any, and if desired, sorting the labeled cells, if any.

The processes of the invention may be used to analyze and/or separate a variety of cell types. For example, it can be used to detect and select hybridoma cell lines that secrete high levels of antibodies.

An exemplary process for the selection of this type of hybridoma cell is the following. The cells are modified to contain a digoxigenin anchor moiety by coupling digoxigenin to the cell via a lipophilic anchor moiety or by chemical coupling. A capture moiety is linked to the cells via a rat anti-kappa or rat anti-lambda monoclonal antibody conjugated to anti-digoxigenin antibody or antibody fragments. The cells with the linked capture moiety are incubated to allow secretion of the monoclonal antibodies. Cells capturing the secreted product antibodies are labeled with the label moiety by incubation with rat anti-mouse IgG1 or IgG2a+b monoclonal antibody. An anti-class antibody that does not recognize the surface bound form of the product is advantageous when the expression product is naturally associated with the cell surface.

Selection of the high secretor cells is carried out in multiple rounds. Each separation process involves the use of a cell separation process, i.e., a quantitative magnetic separation system that distinguishes different levels of bound product, or a FACS. The cells having the highest labeling (eventually normalized on a cell to cell basis using further parameters) are sorted and expanded in culture again. Magnetic and FACS separation can be combined.

FACS sorting is preferentially performed by additionally labeling the cells for amount of capture moiety using a different fluorochrome than that with which the cells are originally labeled, then selecting for cells with a high ratio of amount of product to amount of antibody. Multiple rounds of separation using high cell numbers of $10^7$ to $10^{10}$ cells allows isolation of rare genetic variants showing extraordinarily high levels of production and genetic stability. In order to avoid the selection of cells producing aberrant forms of product, different label moieties may be used during the different rounds of separation.

Using a similar approach, hybridomas with defined specificity may also be detected and selected. By employing a selection process on large cell numbers, rare genetic variants with higher affinity or specificity can be obtained. Class switch variants can be isolated using different anti-class antibodies. Generally, this approach can be used for the isolation of almost any kind of variant of the antibodies with the desired specificity.

The identification and isolation of genes coding for a specific substance, and the isolation of cells producing a specific protein, including specific fusion proteins, cytokines, growth hormones, viral proteins, bacterial proteins, etc., can also be accomplished using the processes of the invention. For example, if it is desirable to select for a cell producing a specific protein, the cells can be genetically modified by the introduction of an expression vector that encodes the protein of interest in a secreted form. The cells are modified by the introduction of a product capture system, including an anchor moiety and a capture moiety specific to the product, and the cells are grown under conditions that allow product secretion. The cells containing the captured product are labeled, and subjected to one or more rounds of separation based upon the presence of label.

Such separation of cells expressing an artificially introduced gene resulting in a secreted product is particularly useful in gene therapy methods where patient cells are removed from the body and transformed with the gene resulting in the secretion of a certain product (e.g., a cytokine). The transformed cells are then isolated from non-transformed cells before being returned to the patient. At present the method used is cumbersome and time-consuming. The cells are transformed not only with the gene expressing the protein of interest but also with a gene expressing a marker is protein. Current techniques utilize β-galactosidase as the marker protein thus, the cells must be cultured in the presence of X-gal and those cells which turn blue are hand-picked and returned to the patient. Not only is this laborious but it results in serious extensions of time prior to treatment of these often gravely ill patients. With the method described herein, the transformed cells can be separated soon after transformation and returned immediately to the patient. The separation can also be based on secretion of the protein of interest rather than a marker protein so as to ensure the cells are transformed and expressing the protein of interest.

The process of the invention may also be used to simultaneously analyze qualitative and quantitative secretion patterns in complex cell mixtures such as, for example, mixtures containing white blood cells, bone marrow cells, suspended tumor cells, or tissue cells. In this case, the cells in the mixture would be labeled with cell specific markers, and would also be labeled with capture moieties for the products to be detected. The cells could also be labeled with bispecific antibodies containing at least one antigen recognition site for the specific cell marker and at least one antigen recognition site for the products to be detected.

After the secretion phase, the cells would be subjected to multiparameter analysis as used in flow cytometry and/or image analysis, and the results analyzed with multi-dimensional statistical methods known in the art, and used in the analysis of flow cytometry and image analysis data. If the analysis is to determine cells specifically reactive with a biological modifier the cells to be analyzed can be exposed to these biological modifiers prior to and/or during the incubation period prior to analysis by flow cytometry or image analysis. Methods such as these are potentially of value for various diagnostic applications in medicine, for example, for measuring levels and types of interleukin production in various cell populations, and for measuring growth factor release in tumor cell populations.

It is contemplated that the reagents used in the detection of secretor cells of desired products may be packaged in the form of kits for convenience. The kits would contain, for example, optionally one or more materials for use in preparing gelatinous cell culture medium, the medium to be used for cell incubation for the production of the desired secreted product; a product capture system comprised of anchor and capture moieties; a label moiety; and instructions for use of the reagents. All the reagents would be packaged in appropriate containers.

The kit may also be formulated to include the following. In this case all the reagents are preferably placed in a single vial to which the cells are added. At least one antibody which is bispecific for a particular cell surface structure or anchor moiety and the product. At least one label moiety and, optionally, biological modifiers.

The label moiety may be a fluorochromated anti-product antibody, which may include, but is not limited to, magnetic bead conjugated, colloidal bead conjugated, FITC, Phycoerythrin, PerCP, AMCA, fluorescent particle or liposome conjugated antibodies. Alternatively the label moiety may be any suitable label including but not limited to those described herein.

Optionally, the kit may include physiologically acceptable buffer. Such buffers are known in the art and include, but are not limited to, PBS with and without BSA, isotonic saline, cell culture media and any special medium required by the particular cell type. Buffers might be used that reduce cross-labeling and increase the local product concentration around the cells. Buffers may include agents for increasing viscosity or decreasing permeability. Suitable agents are described herein. The viscosity of the medium can be reduced before analysis by any method known in the art including, but not limited to, dissolution in a physiologically acceptable buffer, dissolving heat, EDTA, and enzymes. In the absence of added medium cells already suspended in a medium may be directly added to the vial. Suitable cell suspensions include but are not limited to cell lines and biological samples. Biological samples include, but are not limited to, blood, urine and plasma.

Additional structures may be added for catching unbound product to reduce cell cross-contamination thereby reducing the diffusion of products away from the producing cells. These include, but are not limited to, anti-product antibody immobilized to gel elements, beads, magnetic beads, polymers.

Biological modifiers may also be added to the buffer or medium to induce specific secretion. Additional label moieties such as antibodies (magnetically or fluorescently labeled) are also present, including, but not limited to anti-cell surface antibodies to identify cell types, propidium iodide to label dead cells, and magnetic beads to label certain cell types.

In this embodiment, all materials can be placed in a single container such as a vial and the cell sample added. The contents are incubated to allow secretion of a product and subsequent capture of the product and binding of the label moiety to the product. The cells which have secreted and bound product can then be separated and/or analyzed based on the presence, absence or amount of the captured product. Separation may be done by any of the methods known in the art, including, but not limited to, simple dilution, erythrocyte lysis, centrifugation-washing step, magnetic separation, FACS and Ficoll separation. The analysis of the cells may be performed by a variety of methods, including, but not limited to, FACS, image analysis, cytological labeling, and immunoassay.

As shown below, in the examples, cells secreting designated products can be identified and sorted within minutes of incubation in the presence of the specific binding partners. Thus the kits described are suitable for use in diagnostic applications. For instance, suitable diagnostic applications include, but are not limited to, immune disregulations, genetic defects and cancer classification.

The examples described below are provided only for illustrative purposes, and not to limit the scope of the present invention. In light of the present disclosure, numerous embodiments within the scope of the claims will be apparent to those of ordinary skill in the art.

EXAMPLES

Example 1

The purpose of this example was to separate living cells that secrete a given product from a mixture of externally identical cells. The B.1.8. hybridoma cell line and the X63. Ag 8 6.5.3. myeloma cell line were used as the test system. About 60% of B.1.8. cells secrete IgM; the myeloma line secretes no protein. The secreting cells were to be separated from B.1.8. and from mixtures of B.1.8. with Ag 8 6.5.3. cells. To achieve this, a procedure was developed to capture, on the cell surface, a product secreted by the cell, hold the product on the cell surface, and thus label the cell in question. The capture antibodies were attached in two steps: 1) biotinylation of the cells; and 2) attachment of the capture antibody through an avidin-biotin coupling reaction. The labeled cells were then separated from cell mixtures.

Biotinylation of the Cell Surface with Biotinylpalmitoyldextran

The objective was the synthesis of an anchor moiety which is a large macromolecule with biotin groups an a fatty acid group that was to embed itself in the cell membrane.

Synthesis of a Hydrophobic Biotin

A dextran with a molecular weight of $3 \times 10^6$ g/mole was used as the carrier molecule. In order to be able to couple both biotin groups and the fatty acid group to the polysaccharide, reactive primary amino groups first were introduced into the dextran.

Biotinyl groups and a palmitoyl group were then to be introduced to the amino groups of proteins by somewhat modified methods such as those used for coupling biotin and fatty acid esters. FIG. 1 shows the scheme for the introduction of biotinyl and palmitoyl groups onto Dextran.

Synthesis of an Aminodextran

Amino groups were introduced into Dextran molecules by activation with carbodiimidazole and reaction with diaminohexan using standard methods. Aminodextran was obtained from Sigma Corp. and from Molecular Probes (Oregon). An aminodextran with 165±20 amino groups per molecule of $3 \times 10^6$ g/mole was obtained. Polymerization of dextran occurs as a side reaction. The yield of unpolymerized product amounted to 94% of the starting dextran.

A method described by Dubois was used to determine dextran concentrations. 5 µl of an 80% solution of phenol in water was placed in a test tube with 100 µl of the dextran solution to be determined. 1 ml of concentrated sulfuric acid was pipetted quickly into this mixture. After 10 minutes, the formulation was placed in a water bath at 30° C. for 10 minutes longer. The dextran concentration was found by measuring the extinction at 480 nm.

Synthesis of Biotinylaminodextran

Figure 2:
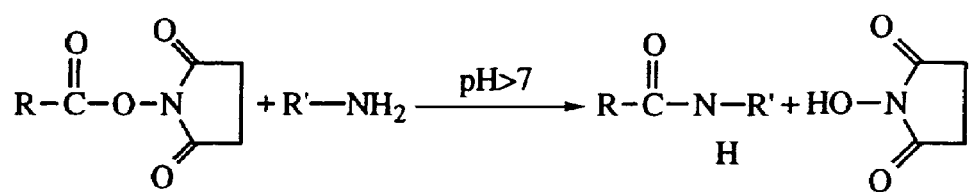
FIG. 2 is a scheme for the reaction of N-hydroxysuccinimide (NHS) esters with primary amino groups in basic form.

The introduction of biotinyl groups onto the dextran was accomplished using D-biotinyl-N-hydroxysuccinimide as the biotinylation reagent. Succinimide groups react effectively with amino groups at pH values above 7. FIG. 2 is a scheme for the reaction of N-hydroxysuccinimide esters with primary amino groups in basic form. The corresponding N-hydroxysuccinimide (NHS) esters were used for introducing both the biotinyl groups and the palmitoyl groups in the dextran. In this Figure, R' stands for dextran, and R stands for either a biotinyl group or for a palmitoyl group.

Synthesis of Biotinylpalmitoyldextran

Palmitic acid groups were coupled to the biotinylated dextran. The reaction was carried out by a slightly modified procedure for coupling palmitoyl groups to antibodies (Huang et al., J. Biol. Chem. 255:8015–8018 (1980)). The coupling occurs similarly to the preceding biotinylation by nucleophilic attack of the amino groups of the dextran on the NHS ester of palmitic acid.

Biotinylation of Cells with Biotinylpalmitoyldextran

The ability of the lipopolysaccharide, biotinylpalmitoyldextran, to bind to cells and thereby biotinylate the cell surface was tested on human lymphocytes and compared with the binding of biotinylaminodextrans lacking palmitoyl groups.

The cells were centrifuged out at 20° C. and incubated for 10 minutes at 37° C. with 1 mg/ml of either biotinyldextran or biotinylpalmitoyldextran in PBS (100 µl for $10^7$ cells). 1 ml of PBS 1% BSA (PBS/BSA) was then added, and after 3 minutes the cells were washed on ice in 14 ml of PBS. The treated cells were taken up in PBS 0.03% sodium azide (PBS/NaN$_3$).

Biotinylation of the cells by biotinyldextran or biotinylpalmitoyldextran was monitored by labeling of the cells with streptavidin-FITC (ST-FITC). More specifically, the treated cells were washed and taken up in 100 µl of PBS/$10^7$ cells. 1 µl of 100 µg/ml ST-FITC in PBS was added and the mixtures were incubated for 5 minutes on ice. The cells were then washed, taken up in 1 ml of PBS/BSA per $10^7$ cells, and the intensity of fluorescence was measured in the FACScan as a measure of biotinylation.

Figure 3A:
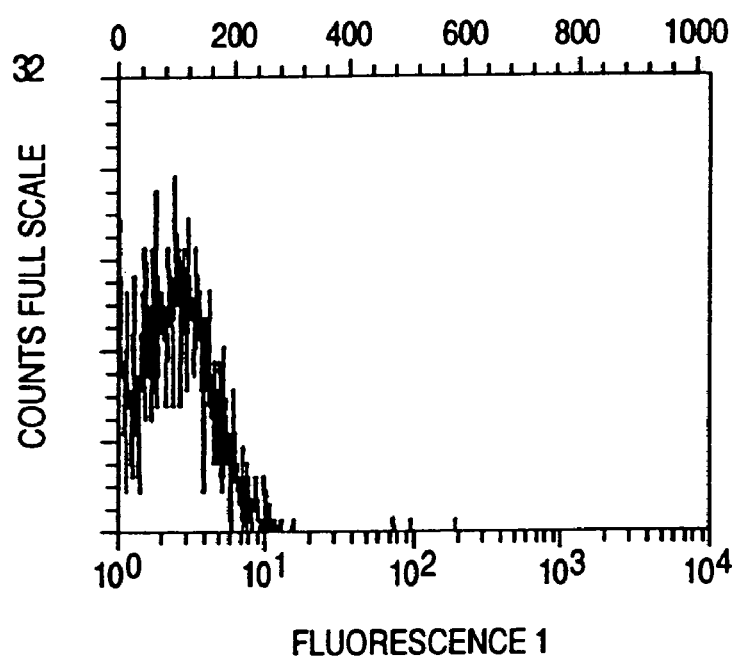
FIG. 3a and FIG. 3b, respectively, are photocopies of traces of the fluorescence activated cell sorting analyses (FACScans) of binding of streptavidin to cells treated with biotinyldextran and biotinylpalmitoyldextran.
Figure 3B:
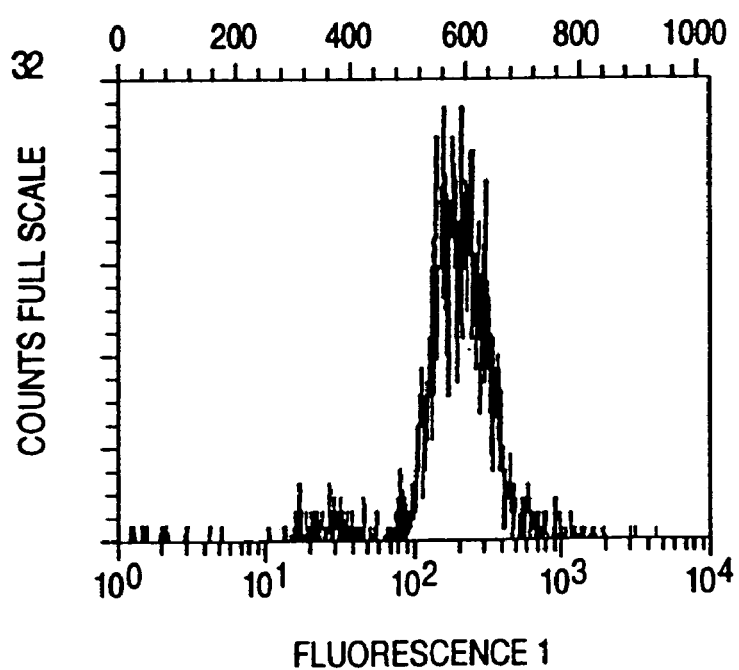

The results of the FACScans of binding of streptavidin to cells treated with biotinyldextran and biotinylpalmitoyldextran are shown in FIG. 3a and FIG. 3b, respectively. As seen from the results, cells incubated with biotinyldextran did not bind ST-FITC. In contrast, cells incubated with biotinylpalmitoyldextran bound large amounts of the ST-FITC.

Figure 4A:
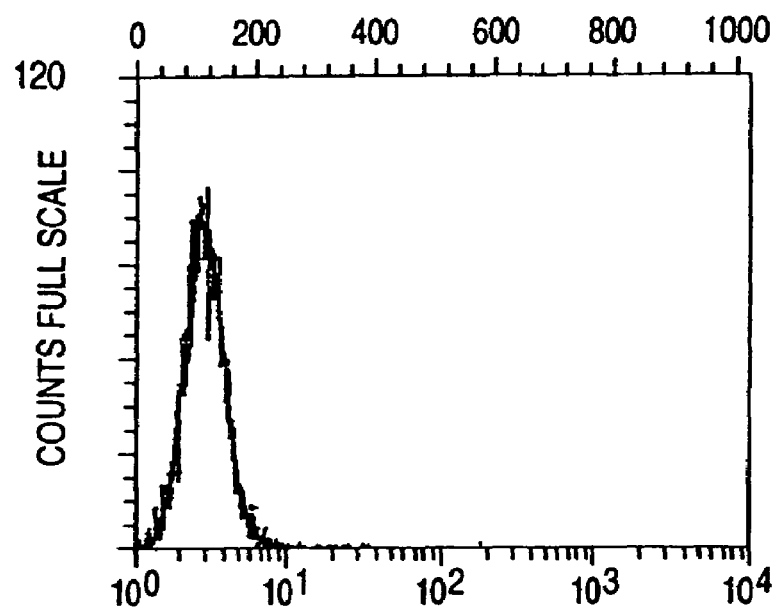
FIG. 4 are photocopies of traces of the FACScan results: a) unbiotinylated cells treated with streptavidin labeled with fluorisothiocyanate (ST-FITC) (negative control); b) cells treated with biotinylpalmitoyldextran and then with ST-FITC; c) cells incubated with biotinyl-anti-$\beta_2$ microglobulin ($\beta_2$m) and treated with ST-FITC.
Figure 4B:
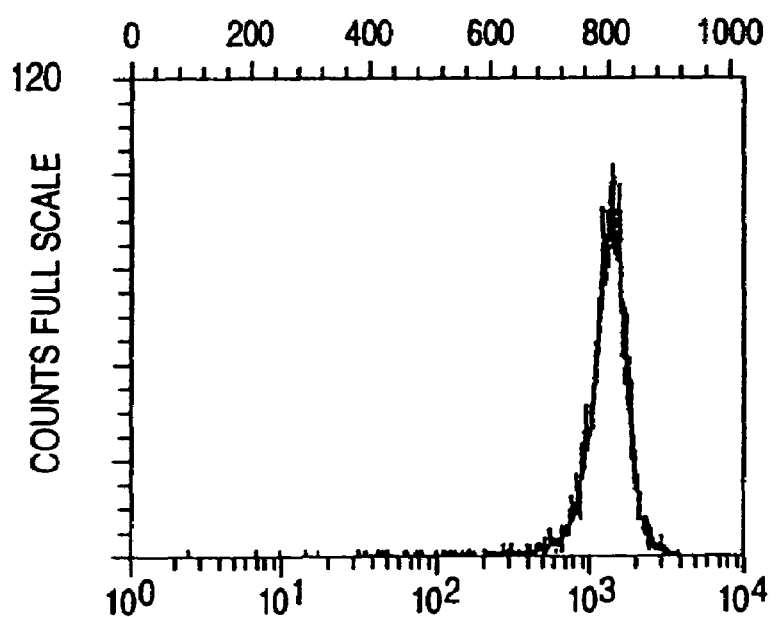
Figure 4C:
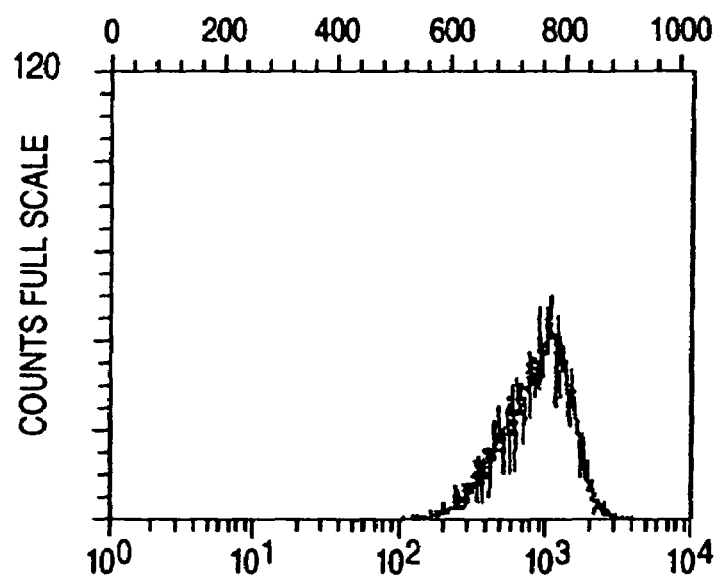

A comparison was made between the amount of ST-FITC bound by cells labeled with biotinyl antibodies directed towards $\beta_2$ microglobulin ($\beta_2$m) and the biotinylpalmitoyldextran labeled cells. The antibody used was $\alpha\beta_2$m, an antibody that binds to $\beta_2$m. FIG. 4 shows traces of the FACScan results: a) unbiotinylated cells treated with ST-FITC (negative control); b) cells treated with biotinylpalmitoyldextran and then with ST-FITC; c) cells incubated with biotinyl-$\alpha\beta_2$m and treated with ST-FITC. The results in FIG. 4 indicate that cells labeled with biotinylpalmitoyldextran are able to bind more streptavidin to the cell surface than an $\alpha\beta_2$m-biotin conjugate.

While antibody labeling of the cell reaches saturation, labeling by biotinylpalmitoyldextran increases linearly with the concentration of the labeling reagent. However, the labeling is limited by injury to the cells when the concentrations of reagent are too high. When biotinylation of the cells was with about 1 mg/ml of biotinylpalmitoyldextran for 10 minutes at 37° C., no change of the cell surface was observed under the microscope; the light-scattering properties of the cell surface, which were measured in the FACScan with forward and lateral scattered light, were unchanged compared to untreated cells. The treated cells maintained viability and could be cultured again.

Coupling of Capture Antibodies to Biotinylated Cells

Capture antibodies were coupled to cells biotinylated with biotinylpalmitoyldextran via an avidin-biotin bridge. In order to accomplish this, the capture antibodies were conjugated with avidin, and the conjugates reacted with the biotinylated cells.

Two antibodies, rat anti-mouse IgM (R33.24.12) and mouse kappa against mouse lambda (LS136) against various epitopes on mouse IgM (lambda) were coupled to avidin.

Avidin is a basic protein with several reactive amino groups. Succinimydyl 4-(N-maleimidomethyl) cyclohexane-1-carboxylate (SMCC) was used to couple avidin to the capture antibodies. SMCC is a bivalent linker molecule whose maleimide group reacts selectively with thiols and whose succinimydyl group reacts selectively with primary amines. The capture antibody was reduced with DTT. DTT is a mild reducing agent that under suitable conditions reduces 1–4 disulfide bridges of an IgG molecule to thiols without destroying the antigen-binding site. A reactive maleimide group was introduced on the amino groups of avidin with SMCC. The maleimide group of avidin was reacted with the SH groups of the reduced antibody. Avidin and capture antibodies were joined in this way through a cyclohexane bridge.

More specifically, 1.5 µl of a 1 molar solution of DTT was added to 1 mg of antibody of the IgG class in 200 µl of PBS containing 5 mM EDTA (PBS/EDTA). After reaction for 1 hour at room temperature, the reduced antibody was placed on a chromatographic separation matrix SEPHADEX™ PD10 column and eluted in 1 ml of PBS/EDTA. The number of thiol groups introduced per antibody molecule was determined. The desirable range is about 2–6 thiol groups per antibody molecule.

Concomitantly, 1 mg of avidin was dissolved in 100 µl of carbonate buffer pH=9.4 and 125 µg of SMCC in 7.5 µl of DMSO were added. After 1 hour at room temperature, the protein was purified on a SEPHADEX™ PD10 column and taken up in 500 µl of PBS/EDTA.

1 mg of the reduced antibody in 1 ml of PBS/EDTA was combined with 400 µg of the activated avidin in 200 µg of PBS/EDTA and allowed to stand overnight at 4° C. The reaction was stopped by adding 5 µl of 1 M N-ethylmaleimide.

Coupling of Avidin-labeled Capture Antibodies to Biotinylated Cells

A mixture of myeloma and hybridoma cells was used. B.1.8. hybridoma cells that secrete IgM and nonproducing X63. Ag 8 6.5.3 myeloma cells were grown at 37° C. in an atmosphere saturated with water vapor. The culture medium contained RPMI and 5% fetal calf serum (FCS), 100 IU/ml of penicillin, and 0.1 mg/ml of streptomycin.

The cell mixture was biotinylated with biotinylpalmitoyl-dextran using the conditions described above.

In order to couple the antibody-avidin conjugates to the biotinylated cells, the biotinylated cells, after washing in PBS/1% BSA, were incubated with an avidin-capture antibody conjugate. 1 µl of a solution of 1 mg/ml of capture antibody-avidin conjugate in PBS was added to $10^7$ biotinylated cells in 100 µl of PBS/NaN$_3$. After 10 minutes on ice, the biotin groups were saturated with capture antibody, and the cells were loaded with capture antibodies.

In order to detect the presence of the avidin-antibody complexes on the cell surface, a fluorescent anti-antibody was used, and the fluorescent labeling detected by FACScan. The labeling of cells corresponded approximately to the labeling of biotinylated cells with fluorescent streptavidin, performed in the same study. A uniform labeling of the cell population was observed; all of the cells carried about the same amounts of capture antibodies on their surfaces.

Testing the Functionality of Capture Antibodies on the Cell Surface

Figure 5:
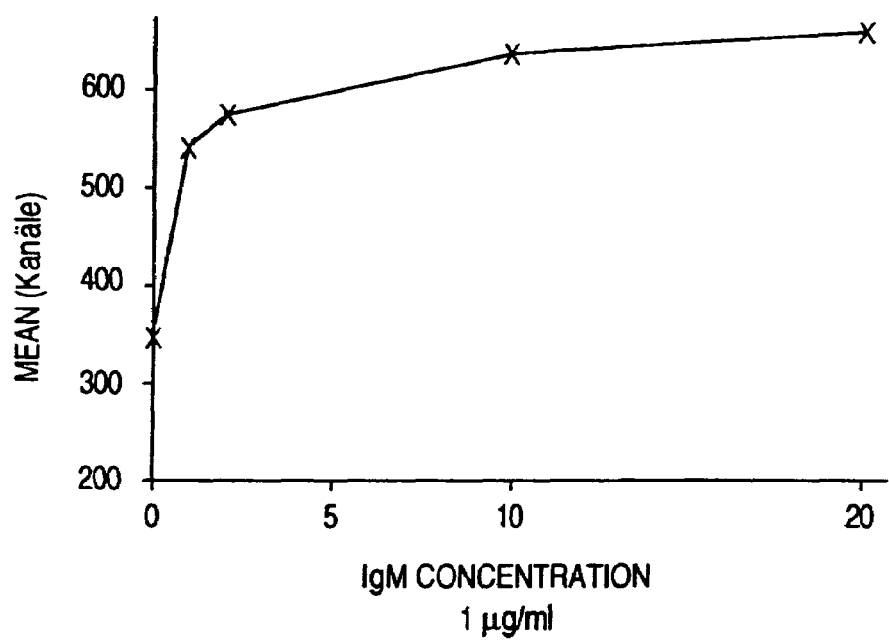
FIG. 5 is a graph showing the titration of the binding of IgM to cells carrying conjugates of biotinylpalmitoyldextran and capture antibodies.
Figure 6A:
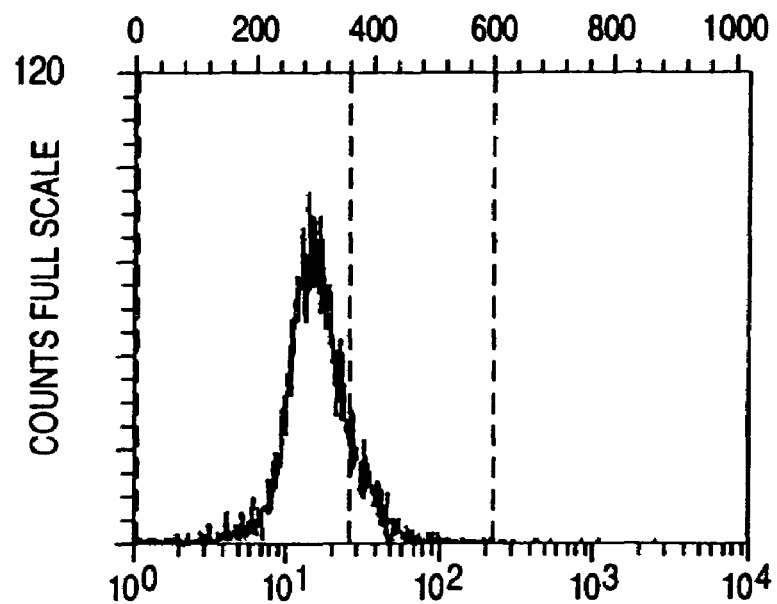
FIG. 6 are photocopies of traces of FACScan results of the capture with time of IgM on cells carrying capture antibody avidin-biotin conjugates. Panels (a), (b), (c), and (d) are the traces at 10 min, 30 min, 1 h, and 2 h, respectively.
Figure 6B:
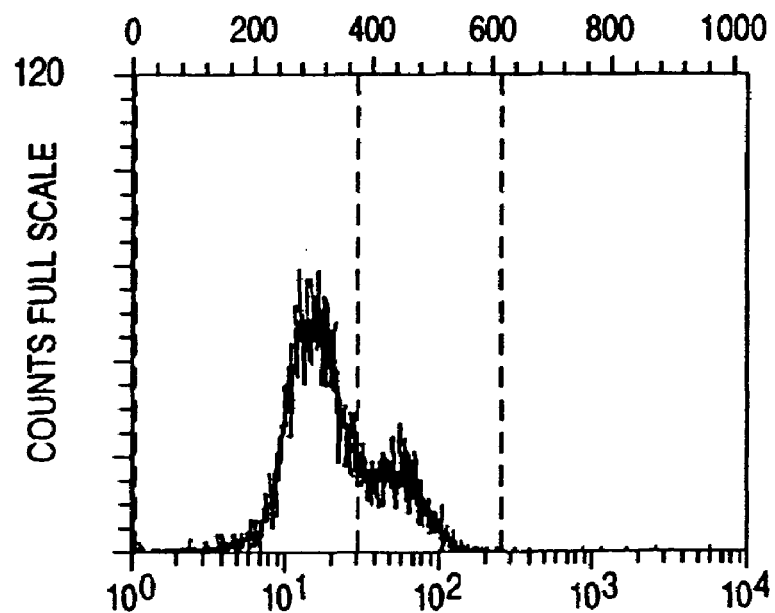
Figure 6C:
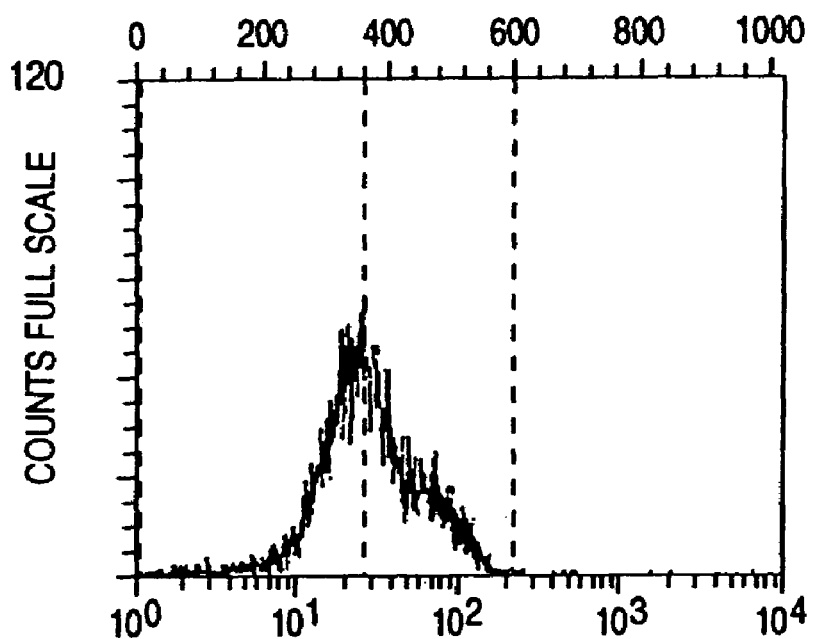
Figure 6D:
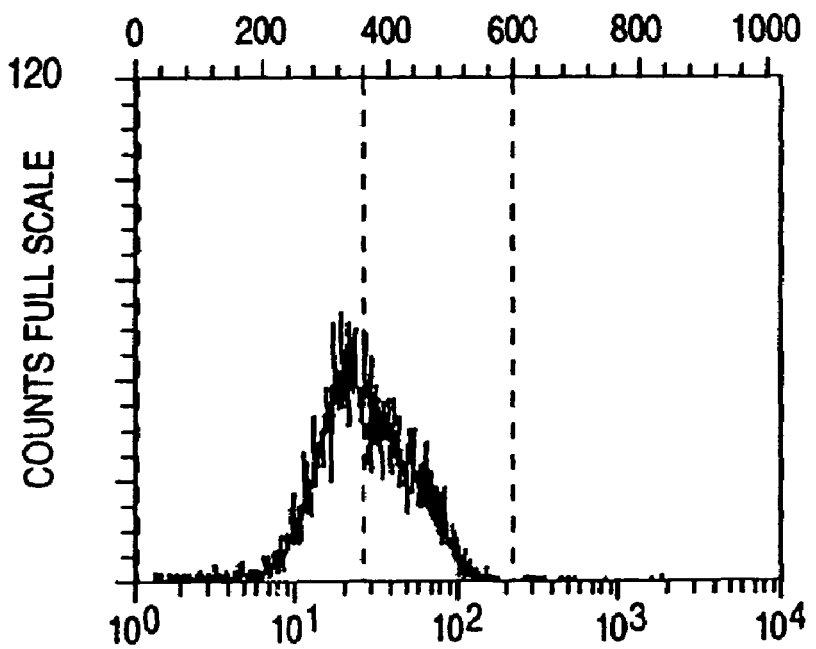

About $10^7$ cells provided with capture antibodies were incubated on ice (so that they secreted no protein) in 100 µl PBS/BSA, with various concentrations of mouse IgM, which is captured by the capture antibodies. After 5 minutes of incubation, the cells were washed and the captured IgM was detected on the cell surface using R-PE conjugate as the antibody label. Detection was in the FACScan. FIG. 5 shows the titration curve. In the figure, the fluorescence of the cells (mean) is plotted against the IgM concentration with which the cells were incubated. These results show that the capture antibody on the cell surface still has intact binding sites. The sensitivity of the capture antibodies to low IgM concentrations in the medium is also recognizable. The titration curve illustrated was obtained using R33.24.12 as capture antibody. The capture antibody LS136 was used for the capture experiments shown later. The latter showed somewhat higher sensitivity to low IgM concentrations in the medium.

Capture of Secreted IgM

A mixture of biotinylated B.1.8. and X63 cells was conjugated with capture antibodies and was kept under a 7.5% CO$_2$ atmosphere at 37° C. for various lengths of time in medium. The IgM captured on its surface was then detected by an antibody label.

FIG. 6 shows the resulting labelings as FACScan illustrations: duration of capture test (6a) 10 min; (6b) 30 min; (6c) 1 h; and (6d) 2 h. Two populations can be differentiated after 30 min, which have captured different amounts of IgM. The difference between the two populations disappears after lengthy incubation because of IgM given off to the medium by the secreting cells, which is taken up by the capture antibodies on the nonsecreting cells.

Capture of Secreted IgM Using a Diffusion Inhibitor

It can be seen from the illustration above that the less strongly labeled cell population also takes up IgM rapidly on its surface. This background labeling comes from secreted IgM in the culture medium that has not been captured by the capture antibodies on the secreting cells. If the capture experiment is carried out in a more viscous medium, this background labeling can be reduced. Culture medium with 2.5% methylcellulose was used; this medium shows a gel-like consistency.

The cells loaded with capture antibodies were mixed in culture medium with 2.5% methylcellulose or 1% methylcellulose. It was unnecessary and superfluous to wash the cells; capture antibody-avidin conjugate not bound to the cells does not interfere. 2 ml of medium was used for $10^7$ cells. To bring the methylcellulose properly into solution, it was admixed with the culture medium one day previously. The medium was preheated to 37° C., the cells were added and were incubated for 25 to 45 minutes at 37° C. with 7.5% CO$_2$. Under these conditions, the hybridoma cells secreted their product. After the incubation time, the high-viscosity medium was diluted with 45 ml of cold PBS/BSA. The cells were centrifuged out at 4° C. and taken up in 100 to 500 µl of PBS/BSA. Remainders of methylcellulose gave the cell suspension an elevated viscosity; neither the cells nor the subsequent labeling steps were harmed by this.

Figure 7A:
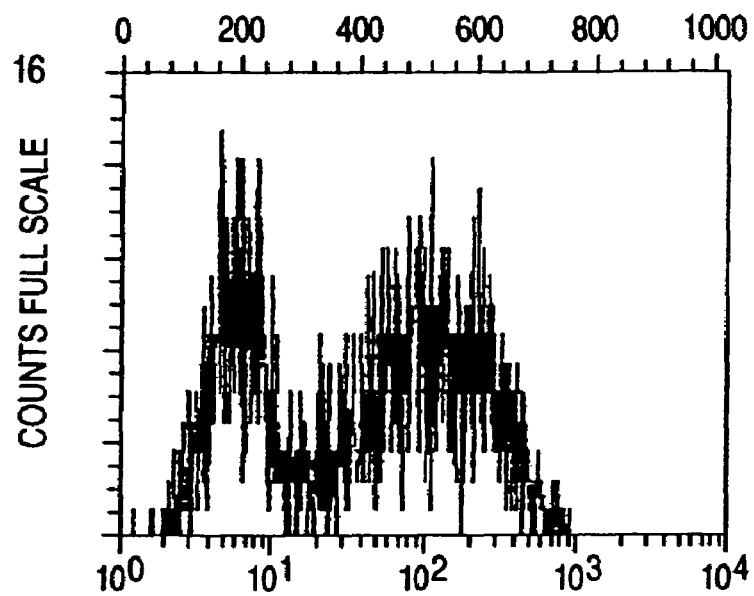
FIGS. 7a and 7b show the capture of antibodies by cells incubated in 2.5% and 1% methylcellulose medium, respectively.
Figure 7B:
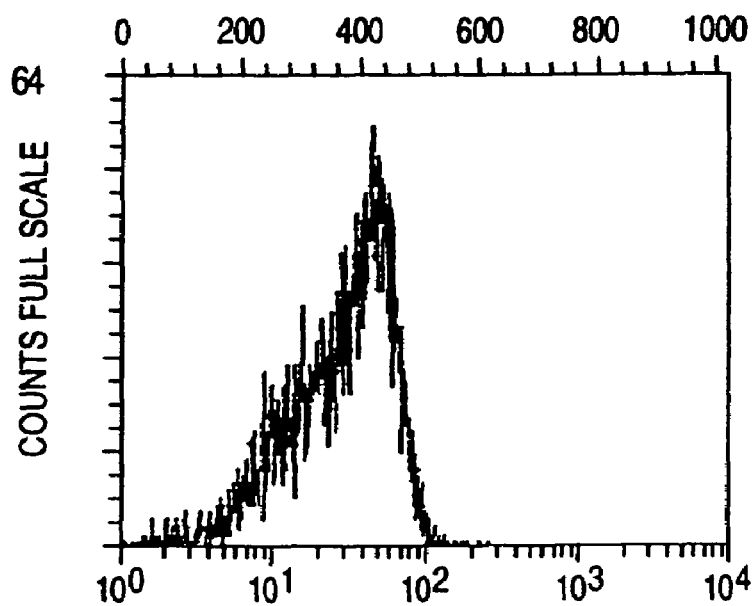

FIG. 7 shows the effect of the concentration of methylcellulose in the medium on capture. The cells in this experiment produced IgM for 35 minutes in 2.5% methylcellulose, and were then washed and labeled with R33.24.12. R-PE. FIGS. 7a and 7b show the capture of antibodies by cells incubated in 2.5% and 1% methylcellulose medium, respectively. The results indicate that the secreting and non-secreting cells were successfully distinguished based on capture in the 2.5% methylcellulose medium.

Double Labeling

To show that the cells carrying IgM on their surface after the capture experiment described above actually are cells secreting IgM, the cells were labeled red on the surface after the capture experiment with R33.24.12. R-PE (visible in the FACScan as Fluorescence 2.), fixed, and labeled green in the cytoplasm with R.33.24.12.-FITC (visible in the FACScan as Fluorescence 1.). The cells labeled twice in this way were examined under the microscope and in the FACScan.

The fact that the cells carrying IgM on their surface after the capture experiment are secreting cells was illustrated by this double labeling as a two-dimensional representation of Fluorescence 1 and 2 in the FACScan. B.1.8. cells after the capture experiment were labeled red on their surface relative to the captured IgM (visible in the FACScan as Fluorescence 2), and were then fixed and labeled green in the cytoplasm relative to IgM (visible in the FACScan as Fluorescence 1). All of the surface-labeled cells are also labeled in the cytoplasm.

The results indicated that all of the cells not producing IgM also belonged to the cell population that were not surface-labeled. The cytoplasm-positive cells were divided into two fractions; on the one hand, a fraction of cells labeled both on the surface and in the cytoplasm. These were apparently secreting cells. On the other hand, a cell fraction was labeled in the cytoplasm but not on the cell surface. Since this population could not be separated by a density gradient medium FICOLL™ gradient (carried out just before fixation), they were not dead cells. Some of the cells in this population were also not labeled as intensely in the cytoplasm as the secreting cells. The broader dispersion of this fraction compared to the two other cell populations was also striking. These cells produced IgM but apparently lost the ability to secrete this protein. The double-labeled cells were observed under the microscope as a control. This examination showed conformity with the outcome of the FACScan representation.

Cell Separation of the MACS

After the capture of secreted IgM with a 1:1 mixture of about $10^7$ B.1.8. and X63 cells, separations were carried out with the magnetic cell sorting system (MACS), using magnetic particles that bind to the captured IgM on the cell surface. The MACS system and magnetic particles were from Miltenyi Biotec GmbH (Germany).

A mixture of IgM-secreting and nonsecreting cells was provided with the matrix for capturing secreted IgM developed in this work and was kept at 37° C. in an atmosphere of 7.5% $CO_2$ for 25 minutes in 5 ml of culture medium with 2.5% methylcellulose. The cells were washed in 45 ml of PBS/BSA. The pellet was treated with a remainder of methylcellulose of gel-like consistency. It was taken up in 500 µl of PBS/BSA and 5 µl of rat anti-mouse IgM magnetic beads (Miltenyi Biotec GmbH) were added. After 5 minutes on ice, 10 µg/ml of R-PE-coupled R33.24.12 antibody was added and the mixture was kept on ice for 5 min longer.

About $10^7$ cells pretreated in this way were placed on a type A1 separating column in the MACS (Miltenyi Biotec GmbH) and the negative fraction was eluted with 10 ml of PBS/BSA at 5° C. After removing the column from the magnetic field, the positive cell fraction was eluted in 10 ml of PBS/BSA.

Cells surface-labeled red relative to IgM are shown in FIG. 8 before and after the separation. The cell suspension prior to separation contained 58.8% unlabeled and 41.2% labeled cells. After the separation, the negative fraction contained 89% unlabeled and 11% labeled cells. The positive fraction contained 23% unlabeled and 77% labeled cells. When the concentration of positive cells after separation is calculated with the formula: concentration factor=(% pos. cells in pos. fraction * % neg cells in original cell mixture)/% pos. cells in the original fraction * % neg cells in pos. fraction), a concentration factor of 4.8 is obtained.

After the separation, the cells could not be labeled with propidium iodide, a dye that selectively labels dead cells, and could again be cultured. The vitality of the separated cell fractions was checked under the microscope one week after the separation. The loss of cells during the separation process was not determined; no relevant losses of cells normally occur in separations in the MACS.

Figure 8A:
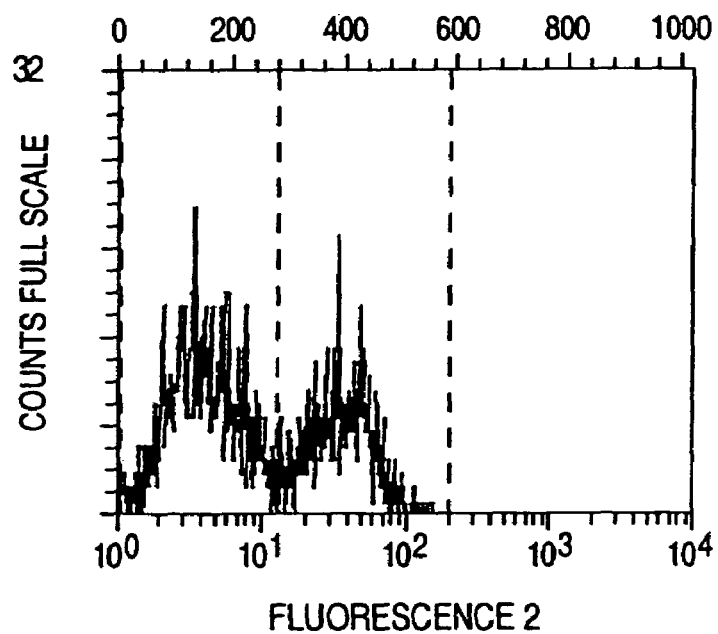
FIG. 8 is a FACScan representation of labeled cells before and after separation based on capture of secreted antibodies in 2.5% methylcellulose containing medium. The cells are shown in the FIG. 8a before separation.
FIG. 8b shows the negative fraction after the separation.
FIG. 8c shows the positive fraction after the separation.
Figure 8B:
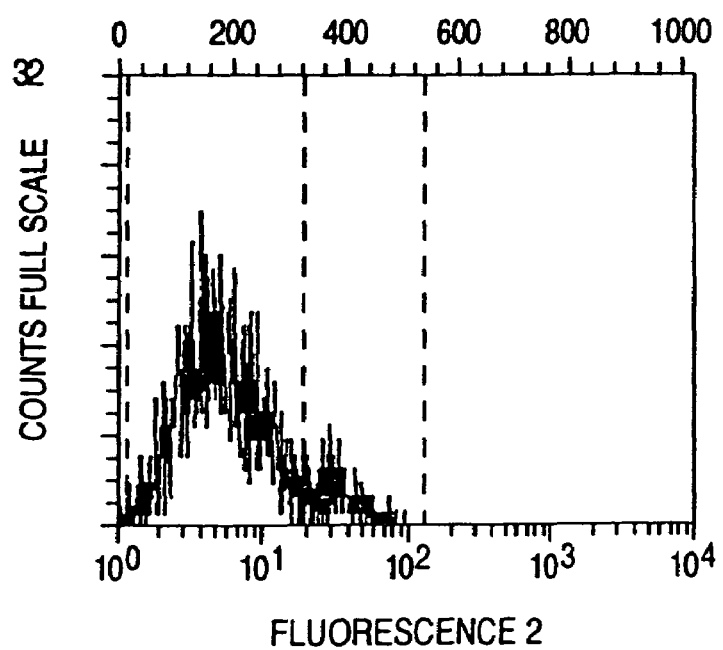
Figure 8C:
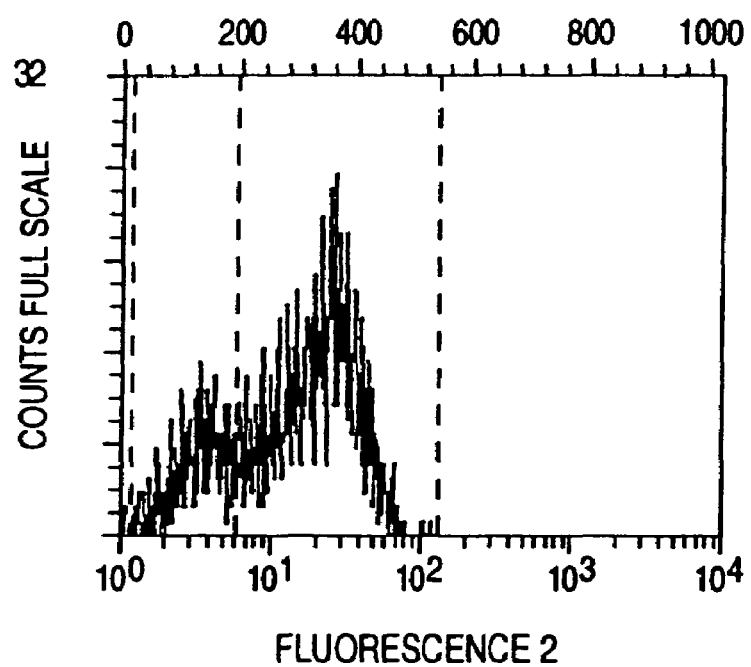

FIG. 8 is a FACScan representation of labeled cells before and after separations. After capturing secreted IgM, the cells were labeled relative to IgM on the surface and were separated in the MACS with magnetic particles relative to IgM. The cells are shown in the FIG. 8a before separation. FIG. 8b shows the negative fraction after the separation. FIG. 8c shows the positive fraction after the separation. If the cells to the right of the broken line are considered to be labeled and those on the left of it to be unlabeled, the cell fractions contained the following amounts of labeled and unlabeled cells:

|  | % neg. | % pos. |
|---|---|---|
| Cells before separation | 58.8 | 41.2 |
| Negative fraction after separation | 89 | 11 |
| Positive fraction after separation | 23 | 77 |

The studies described above included the following general techniques.

Antibody Labeling of Cells

The cells were taken up in PBS/BSA and pelleted by centrifugation. The supernatant was removed by suction, and the pellet resuspended in the antibody labeling solution. 100 µl of labeling solution containing 10–100 µg/ml of antibody in PBS/BSA 0.1% $NaN_3$ was used per $10^7$ cells. The coupling reaction was incubated 5 minutes on ice. The cells were then washed.

Ficoll Gradient Centrifugation

Ficoll gradient centrifugation was used to remove dead cells. The cell suspensions were carefully underlayered with 5 ml of Ficoll (Pharmacia LKB, Uppsala, Sweden) and were then centrifuged at 2500 rpm at room temperature. Living cells remained resting on the Ficoll cushion and were removed by suction.

Cytoplasm Labeling 0.5% saponin and 10 µg/ml of labeling antibody were added to the fixed cells in PBS/BSA. Saponin produces reversible channels about 10 nm in diameter in the cell membrane, so that the antibodies can penetrate into the cells. After a reaction time of 1 hour the cells were taken up in PBS/BSA 0.5% saponin (1 ml/$10^6$ cells). After 30 minutes, the cells were washed and taken up in saponin-free PBS/BSA.

Antibody Used

R33.24.12., a monoclonal rat anti-mouse antibody, coupled both to R-PE and to fluorescein, was obtained from stocks of the Immunobiological Department of the Genetic Institute of Cologne. The optimal labeling concentrations were titrated. The R-PE conjugate of this antibody was used to label the captured IgM on the surface of secreting cells, and the fluorescein conjugate was used for cytoplasm labeling. LS136, a mouse IgG kappa against mouse lambda is used as the capture antibody (the IgM to be captured is of the lambda allotype). LS136 likewise originates from the internal production of the Immunobiological Department.

Example 2

This example demonstrates the effect of carrying out the secretion phase in a gelatinous medium as compared to a high viscosity medium on the capture of secreted product by cells containing a biotin anchor moiety linked via avidin to the capture moiety.

Chemical Biotinylation of Cells Using NHS-LC-Biotin

A mixture of B.1.8. and X63 cells was chemically biotinylated by the following procedure. Cell suspensions containing $10^7$ to $10^8$ cells were centrifuged, the supernatant removed, and the pellet resuspended in a solution of 200 µl PBS pH 8.5, containing 0.1 to 1 mg/ml NHS-LC-Biotin (Pierce, Rockford, Ill., U.S.A.). After incubation for 30 minutes at room temperature the cells were washed two times extensively with 50 ml PBS/BSA. Labeling with avidin conjugate was within 24 hours of the biotinylation.

Linkage of the Biotinylated Cells to Capture Antibodies with Avidin

The cells biotinylated by reaction with NHS-LC-Biotin were labeled with an avidin conjugate of LS136 (concentration of 30 µg/ml) for 30 minutes on ice and washed.

Secretion and Product Capture in Gelatinous Medium and in High Viscosity Medium

The biotinylated-avidin treated cells were incubated 1 hour at 37° C. under 7.5 $CO_2$ in three different media, washed and labeled with a fluorescein conjugate of R 33.24.12 (10 µg/ml) for 10 minutes on ice, washed and analyzed using flow cytometry (FACScan) for determination of the amount of bound R 33.24.12. R 33.24.12 is a fluorescein conjugate of the anti-product antibody. The three different media used during the incubation were: (1) cell culture medium, RPMI, 5% FCS; (2) RPMI, 5% FCS, supplemented with 40% BSA (Fluka, Switzerland); and (3) RPMI, 5% FCS, supplemented with 20% BSA and 20% gelatin (Type B from bovine skin approx. 225 bloom, Sigma Chemical Co.) as a gelatinous diffusion inhibitor. The results are shown in FIGS. 9, 10, and 11.

Figure 9A:
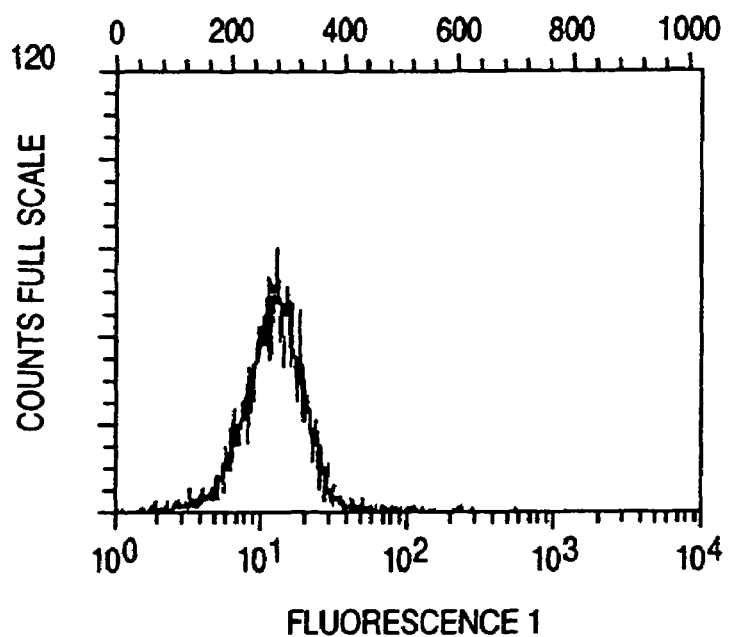
FIG. 9a are photocopies of traces of FACScan results showing the effect of different added substances in the culture medium during the secretion phase.
Figure 9B:
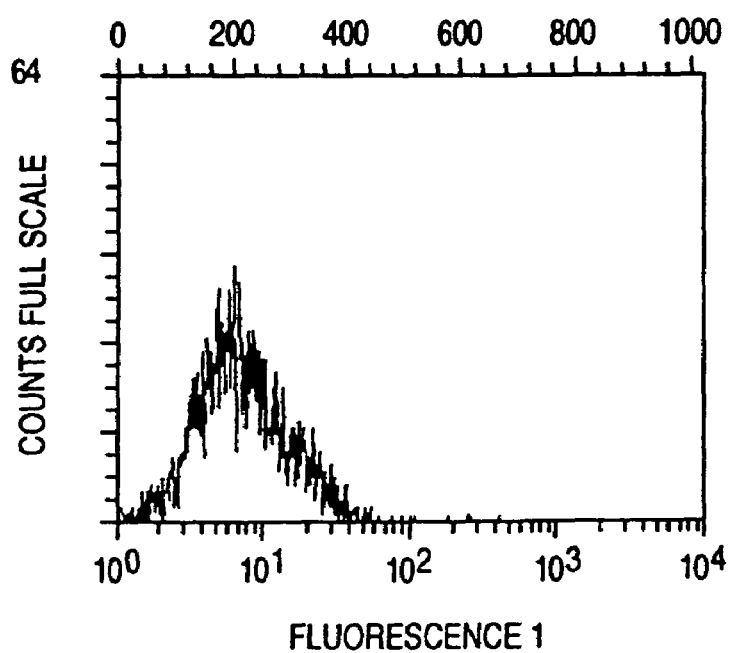
Figure 9C:
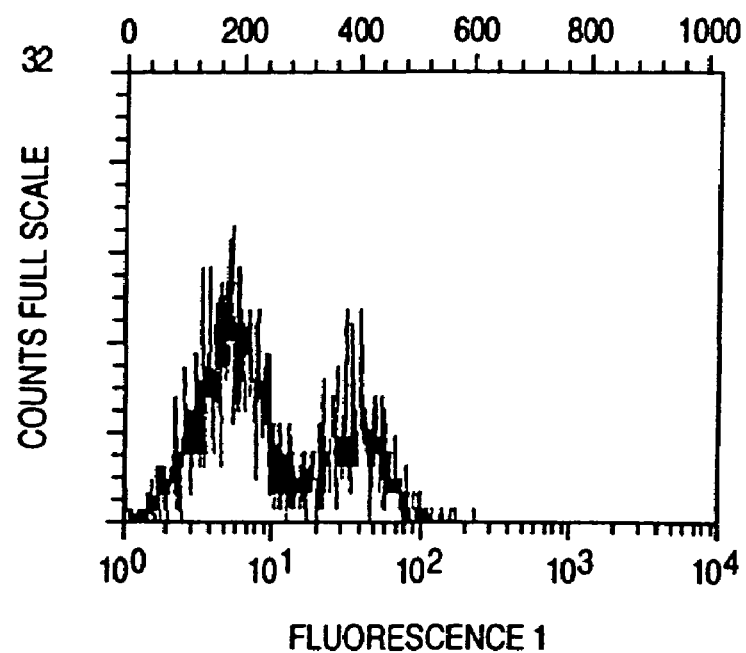
Figure 10A:
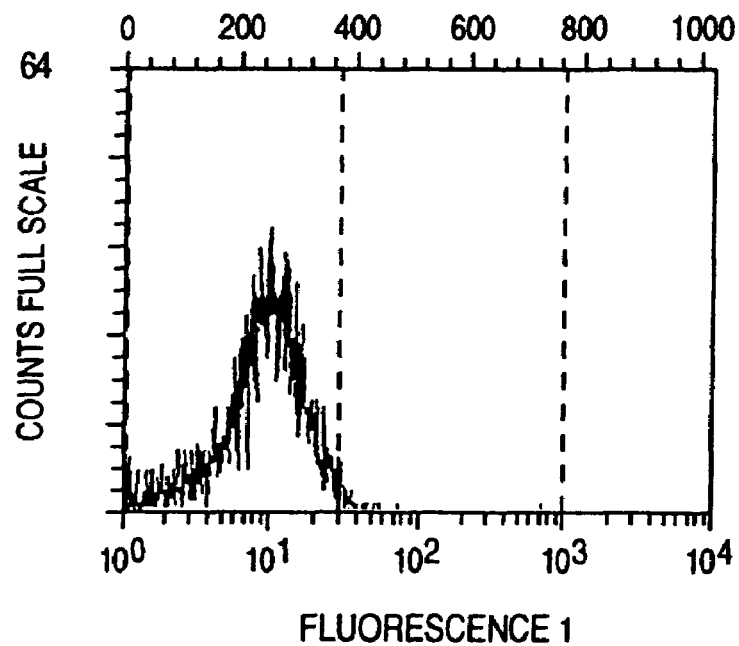
FIGS. 10 and 11 are FACScan representations of labeled cells after labeling with capture antibody (10a, 11a), after the secretion phase (10b, 11b), and after magnetic separation, wherein (10c, 11c) are the magnetic fraction, and (10d and 11d) are the nonmagnetic fraction.
Figure 10B:
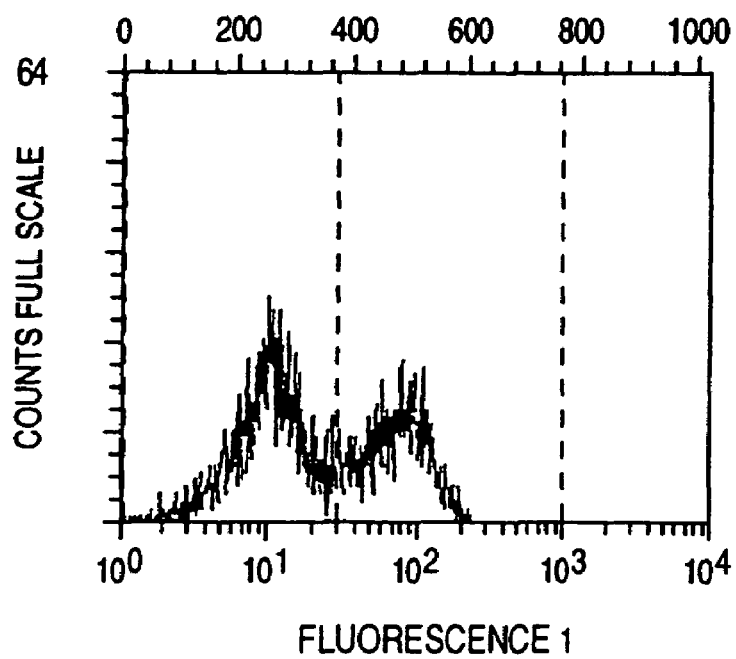
Figure 10C:
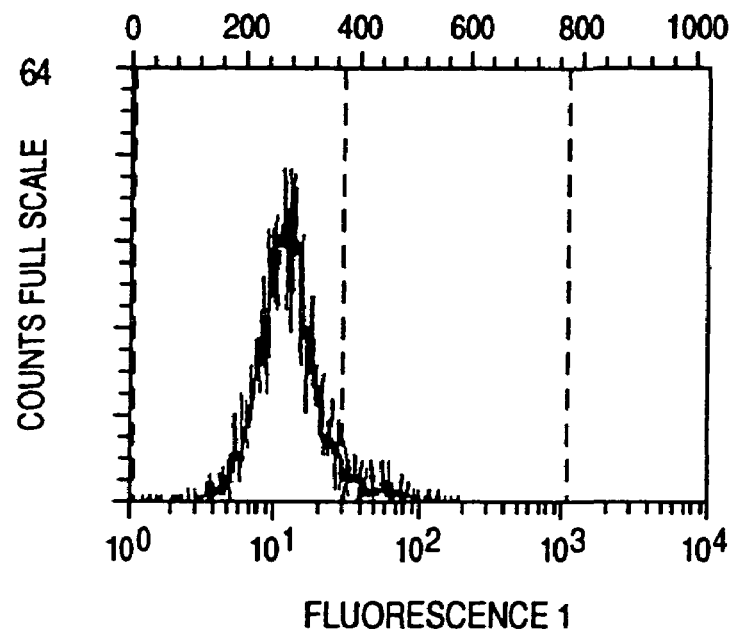
Figure 10D:
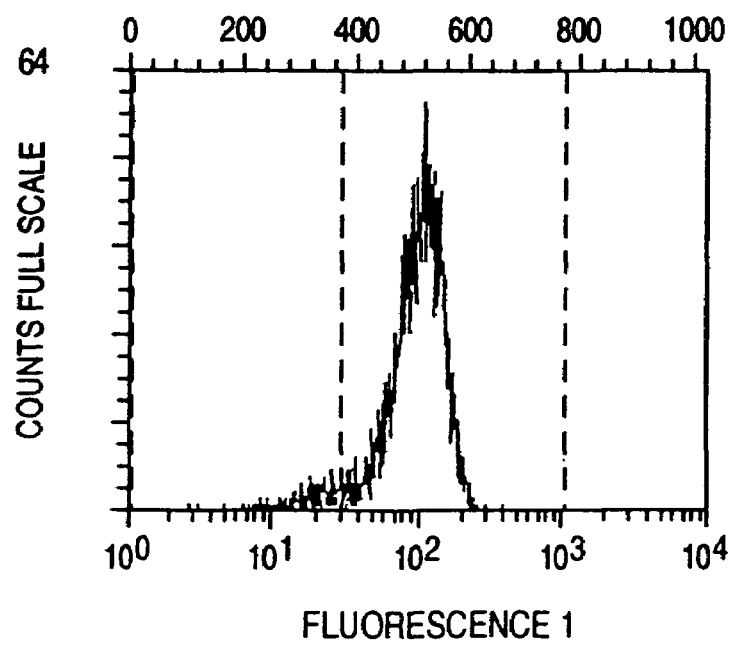

FIG. 9a shows the distribution of labeling of the cells incubated in RPMI, 5% FCS (i.e., without a diffusion inhibitor). The entire cell population is shifted towards higher fluorescence, thus no separation in distinct cell populations can be resolved. FIG. 9b shows the distribution of labeling of cells incubated in RPMI, 5% FCS supplemented with 40% BSA. This BSA medium is a high viscosity diffusion inhibitor. Compared to FIG. 9a, it shows that incubation in this medium led to less background labeling. FIG. 9c shows the distribution of labeling of the cells incubated in RPMI, 5% FCS, supplemented with 20% BSA and 20% gelatin. Using this medium two cell populations, secretors and nonsecretors can be identified. Compared to the cells incubated in the other two media as indicated in FIGS. 9a and 9b, the amount of fluorescence on the secretor population is significantly increased.

This example shows that while a viscous medium such as a high BSA medium will decrease capture of secreted product by non-producer cells, incubation during secretion in a gelatinous medium results in significantly increased labeling of the producer cells with a concomitant lowering of capture non-producer cells. This amplification effect on capture allows the labeling of cells producing lower levels of product and/or allows the use of lower affinity antibodies for the capture of the secreted product. The gelatinous medium appears to result in an increased concentration of the product in the vicinity of the secreting cells while not inhibiting the speed of the capture reaction. When gelatinous media with a cutoff limit lower than the molecular weight of the product is used in the medium, the secreted molecules may concentrate in the gap between cell and medium, resulting in higher local concentrations and more efficient labeling of the secreting cells.

Cell Separation Using MACS

A mixture of B1.8 and X63 cells were chemically biotinylated and labeled with LS136-avidin, as described above. A control sample was taken and stored on ice. The remaining cells were allowed to secrete for 1 hour in 6 ml gelatinous RPMI medium containing 23% gelatin, 18% BSA and 5% FCS. The gel was quickly dissolved in 20 ml of 42° C. PBS, followed by the rapid addition of 30 ml ice-cold PBS and washing in a cooled centrifuge. The cells and the control sample were labeled for 10 minutes on ice with rat anti-mouse IgM microbeads (Miltenyi Biotec GmbH, labeled with goat anti-mouse fluorescein (SBA, Birmingham, Ala.) and washed once. The cells were then separated on an A2 column using a MACS magnetic cell sorter. Separation was performed according to the manufacturer's instructions. The control sample, unseparated sample, and magnetic and non-magnetic fractions were analyzed by Flow Cytometry (FACScan) (Becton Dickinson, San Jose, Calif., USA).

Figure 11A:
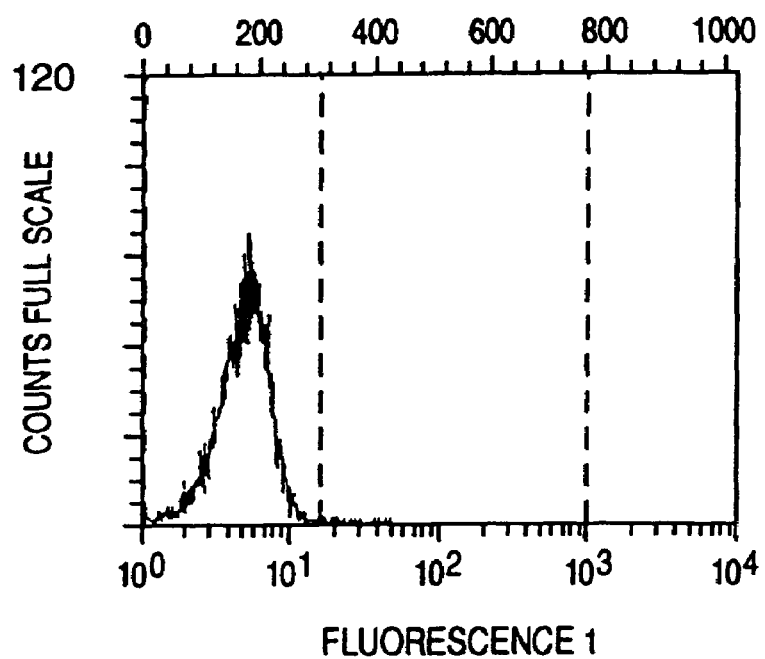
Figure 11B:
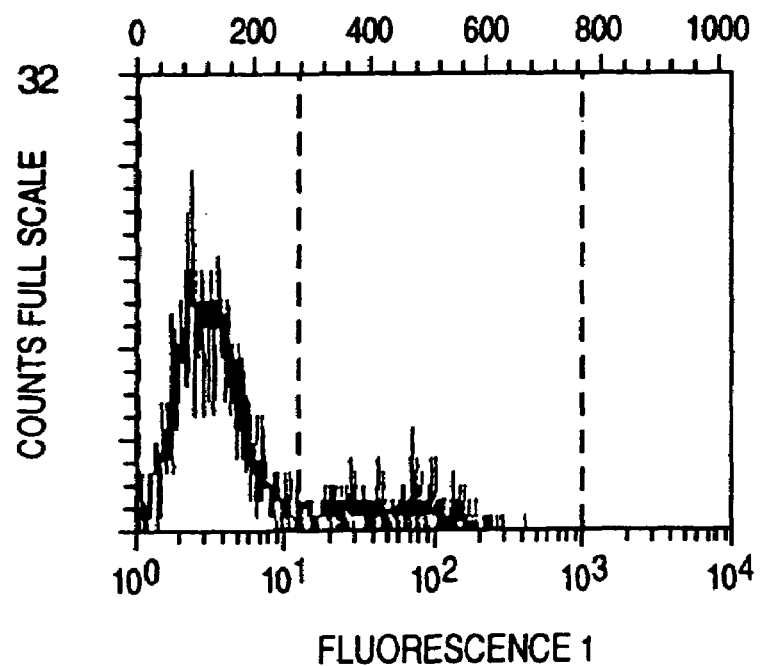
Figure 11C:
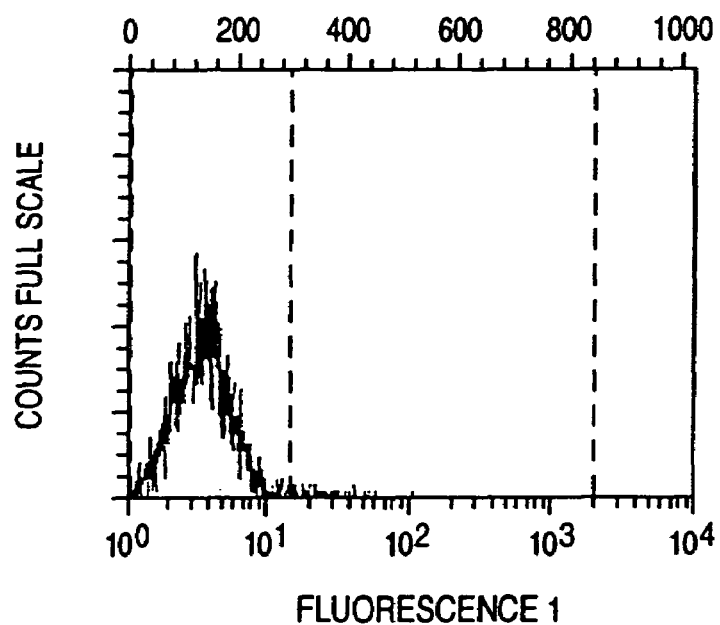
Figure 11D:
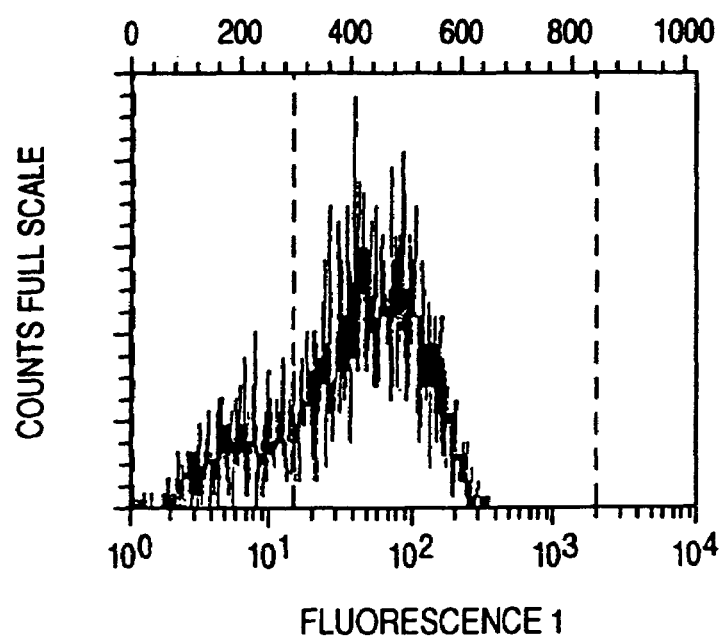

FIG. 11a shows the fluorescence distribution of the control sample. As seen in the figure, almost no detectable surface labeling was detected on the cells (0.6% in area between dotted lines (positive window)). FIG. 11b shows the fluorescence distribution after secretion and fluorescent labeling, prior to magnetic separation. Approximately 14.2% of the cells are in the positive window and are putative secretors. FIG. 11c shows the fluorescence distribution of the non-magnetic fraction after magnetic separation. Nearly all positive cells are retained in the magnetic column (2% of the cells in positive window). FIG. 11d shows the fluorescence distribution of the magnetic fraction. The population of positive cells is highly enriched (80.3% in positive window). It should be noted that the purity of the cell population can be expected to be higher than shown in the FACScan analysis because of instrument limitations. The enrichment rate can be calculated to greater than 24.

FIGS. 10a to 10d show a similar experiment as in FIGS. 11a to 11d, except that a higher proportion of B1.8 to x63 cells was used. Medium during the secretion phase was RPMI containing 25% gelatin and 2.5% FCS. The percentage of cells in the positive window was 1.3% (control), 41.2% (after secretion), 6.6% (non-magnetic fraction), and 92.9% (magnetic fraction). The enrichment rate for positive cells in this example can be calculated to be greater than 18.7, and the depletion rate greater than 9.9.

Example 3

The following describes a method to measure the absolute amount of secretion and to compensate for different amounts of capture moiety on the cell surfaces.

During the secretion phase the cells are exposed to a low concentration of tagged product supplied with the medium; the tagged product binds to but does not saturate the product binding sites on the cells. Incubation during this phase causes both the secreted product and the tagged product to bind to the cells. The cells are then subjected to labeling with the label is moiety specific for the product (both tagged and secreted). Measurement of the tag using one parameter, and the total product in the other parameter, the amount secreted by a cell is normalized, and the different amounts of capture antibody on the cells in the mixture is compensated for.

Example 4

Immunofluorescence Analysis of Live Cells for Secreted Cytokines

This example describes an immunofluorescence method for the analysis of live cells for secreted cytokines. More particularly, this example describes the identification and separation of mouse spleen cells secreting interferonγ (IFNγ). In general, this example involves creating an artificial affinity matrix on the surface of live cells by biotinylation of cell surface proteins and incubation with an avidin-conjugated anti-cytokine antibodies. The cells are incubated in a medium of high viscosity to prevent diffusion of secreted products between secreting and non-secreting cells and allowed to secrete. Secreted cytokines caught on the cell surface are labeled with digoxigenin (DIG) conjugated anti-cytokine antibodies and stained using fluorochromated anti-DIG antibodies. Cells labeled in this manner can then be further characterized for surface marker and sorted by MACS or FACS for functional assays. Combining this method with the intracellular detection of cytokines allows correlation of intracellular accumulation and secretion of cytokines at the level of single cells.

Detection of IFNγ-Secreting Murine Spleen Cells

BALB/c mouse spleen cells (SC) were stimulated with 2 µg/ml *Staphylococcus aureus* enterotoxin B (SEB; Sigma) for about 40 hours at $2 \times 10^6$ cells/ml in RPMI 1640. The cells were then spun down for 10 min at 300 g. The pellet was resuspended in 200 µl NHS-LC-biotin (1 mg/ml; Pierce) in PBS, pH 8.4, and then incubated for 15 min at room temperature. The cells were washed once with PBS with 0.5% BSA (PBS/0.5% BSA), put in another tube and washed a second time with PBS/0.5% BSA.

The cells were resuspended in 200 µl PBS/0.5% BSA with 0.02% $NaN_3$ (PBS/0.5% BSA/$NaN_3$) and unconjugated anti-mouse IFNγ R46A2 (control) was added until a final concentration of 10 µg/ml was achieved. In the test samples avidin-conjugated anti-mouse IFNγ AN18.17.24 was added to achieve a final concentration of 25 µg/ml. The cells were incubated for 5 min at 4° C. Next, the cells were put into Petri dishes in 40% gelatin (75 Bloom; Sigma) in RPMI 1640 (37° C.) at $10^6$ cells/ml for 10–60 minutes at 37° C. and 7.5% $CO_2$.

A 1.5 times volume of PBS (37° C.) was added and the cells put in a 50 ml tube with 2 volumes of PBS (12° C.). These cells were then spun down for 10 minutes at 300 g. The pellet was resuspended in 100 µl DIG-conjugated R46A2 (10 µg/ml) in PBS/0.5% BSA/$NaN_3$, incubated for 10 min at 4° C., and then washed with PBS/0.5% BSA/$NaN_3$. The pellet was next resuspended in 200 µl FITC conjugated sheep anti-DIG antibody (2 µg/ml) in PBS/0.5% BSA/$NaN_3$, incubated for 10 minutes at 4° C., and washed with PBS/0.5BSA/$NaN_3$. The FACS analyses are presented in FIGS. 13 and 14. Optionally, surface labeling, fixation and intracellular labeling of the cells can be performed and resuspended in PBS/0.5% BSA/$NaN_3$.

Results

Figure 12A:
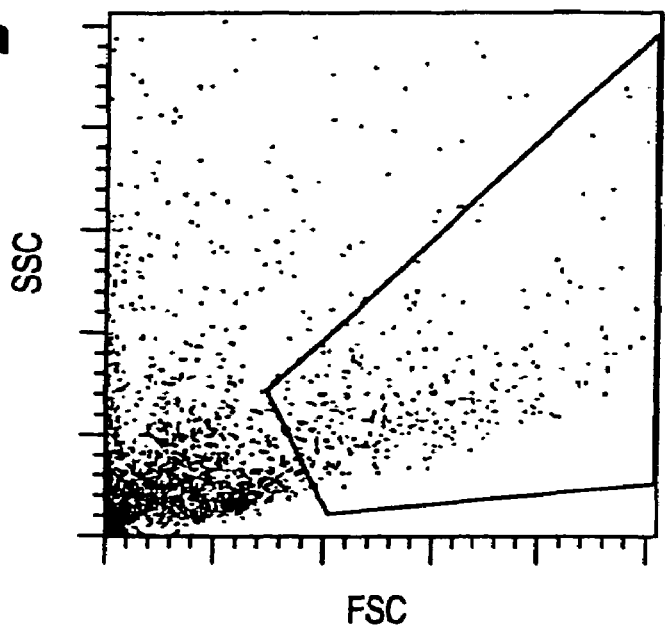
FIG. 12 shows the gating for FIGS. 13 and 14 of mouse spleen cells for FACS analysis. 12a is the forward scatter (FSC) v. side scatter (SSC) plot. 12b shows propidium iodide (PI) v. fluorescence 2. The area enclosed by the lines shows the cells gated for further analysis (blast cells, living).
Figure 12B:
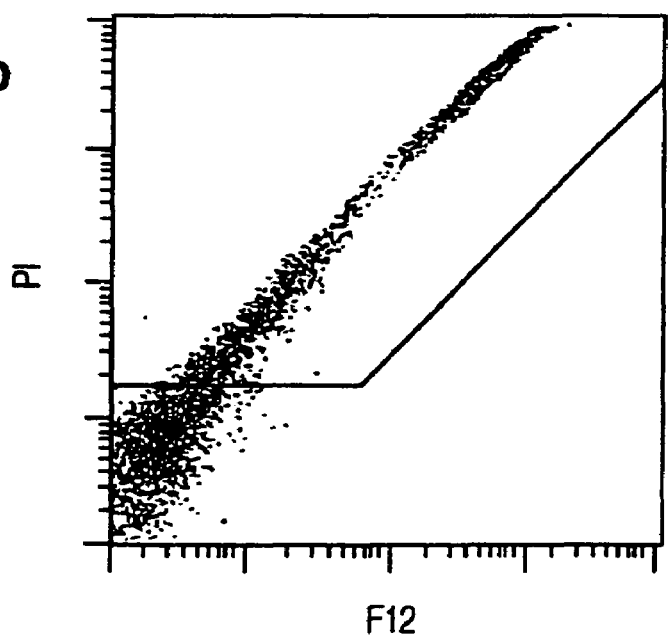
Figure 13A:
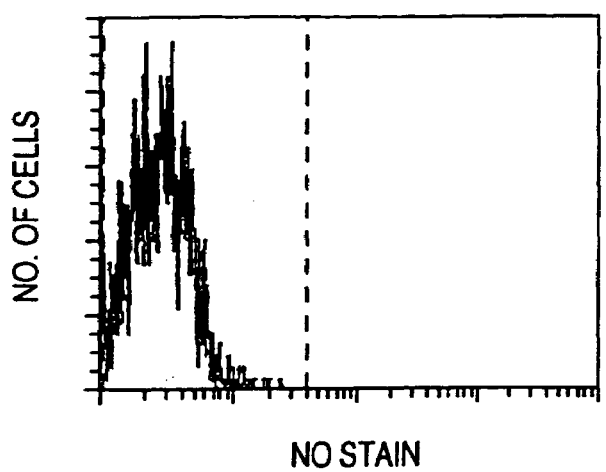
FIG. 13 is a compilation of FACS analyses of FITC labeled cells. 13a is a scan of unlabeled cells. 13b is a scan of cells incubated with ST-FITC before biotinylation. 13c is a scan of cells labeled with ST-FITC after biotinylation. 13d is a negative control showing a scan of cells after biotinylated cells stained with an antibody coupled to FITC specific for rat IgG (GaRIgG-FITC) but which have not been exposed to the avidinated catch antibody (rat) (catch-ab-avidin). 13e is a scan of cells exposed to catch-ab and goat anti-rat IgG-FITC (GaRIgG-FITC).
Figure 13B:
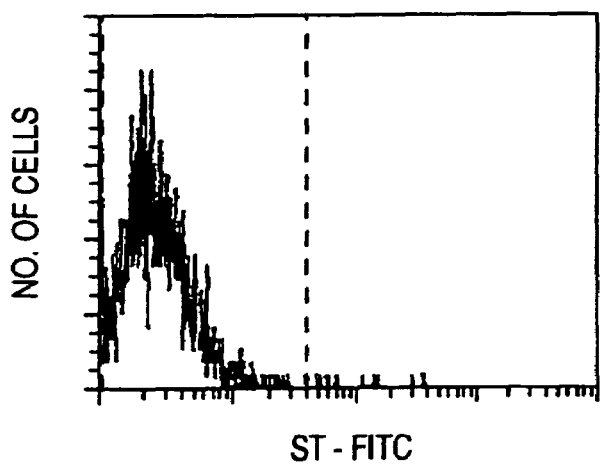
Figure 13C:
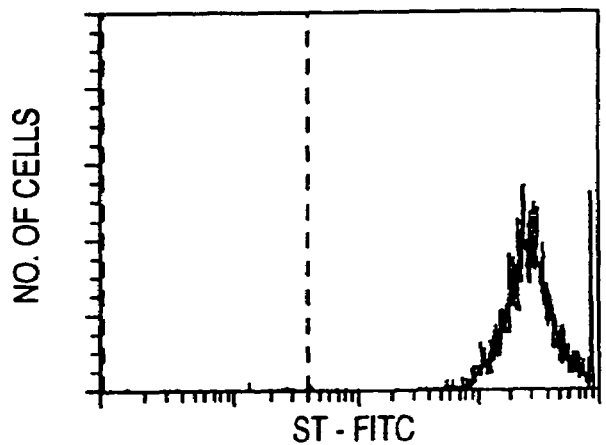
Figure 13D:
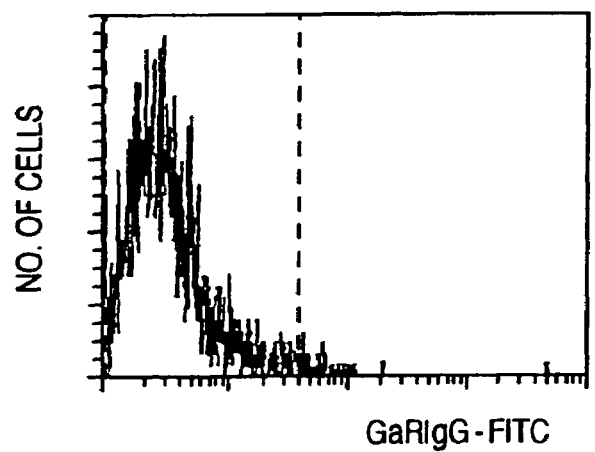
Figure 13E:
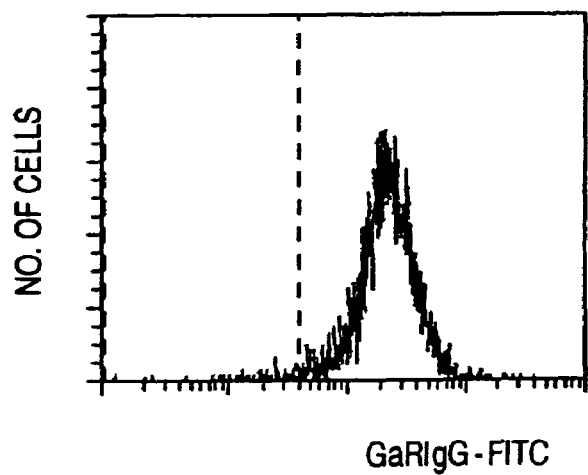

Secretion of IFNγ has been analyzed in mouse spleen cells stimulated in vitro with SEB for 41 hours by flow cytometry. Since IFNγ is produced only from large activated cells (blasts), gating on live blasts was done according to light scatter properties and propidium iodide (PI) labeling (FIG. 12). Biotinylation of cell surface proteins was controlled by labeling with ST-FITC, loading with the catching antibody, by labeling with FITC conjugated goat anti-rat IgG (FIG. 13). FIG. 13a depicts the distribution of unlabeled cells. FIG. 13b depicts the ability of ST-FITC to label cells before biotinylation. Note that the cells are not nonspecifically labeled by ST-FITC. FIG. 13c depicts the ability of ST-FITC to label biotinylated cells. Note that the cells are completely labeled. FIG. 13d depicts labeling of cells that have not been labeled with catch-ab with goat anti-rat IgG labeled with FITC (GaRIgG-FITC). FIG. 13d shows that there is no nonspecific binding of the labeling antibody to the cells. FIG. 13e depicts labeling of cells labeled with avidinated catch-ab with GaRIgG-FITC. FIG. 13e indicates that the catch-ab binds completely to the cells.

As negative control, cells without catch-ab were incubated for 90 min in high density medium (HDM, 40% gelatine in RPMI) and labeled against IFNγ (FIG. 14). As high control, cells with catch-ab incubated for 40 min in HDM were further incubated in IFNγ containing supernatant for 10 min at 4° C. and then labeled against IFNγ (FIG. 14). Among the SEB-stimulated murine SC, labeled with catch-ab, an increasing number of IFNγ secreting cells was detected after incubation in HDM depending on the incubation time (FIG. 14). Additional surface labeling identified these IFNγ secreting SC as CD4+ and CD8+ T cells. The SEB-stimulated T cell blasts secrete varying amounts of IFNγ resulting in a wide distribution of fluorescence intensity (FIG. 14).

Figures 14A, 14B:
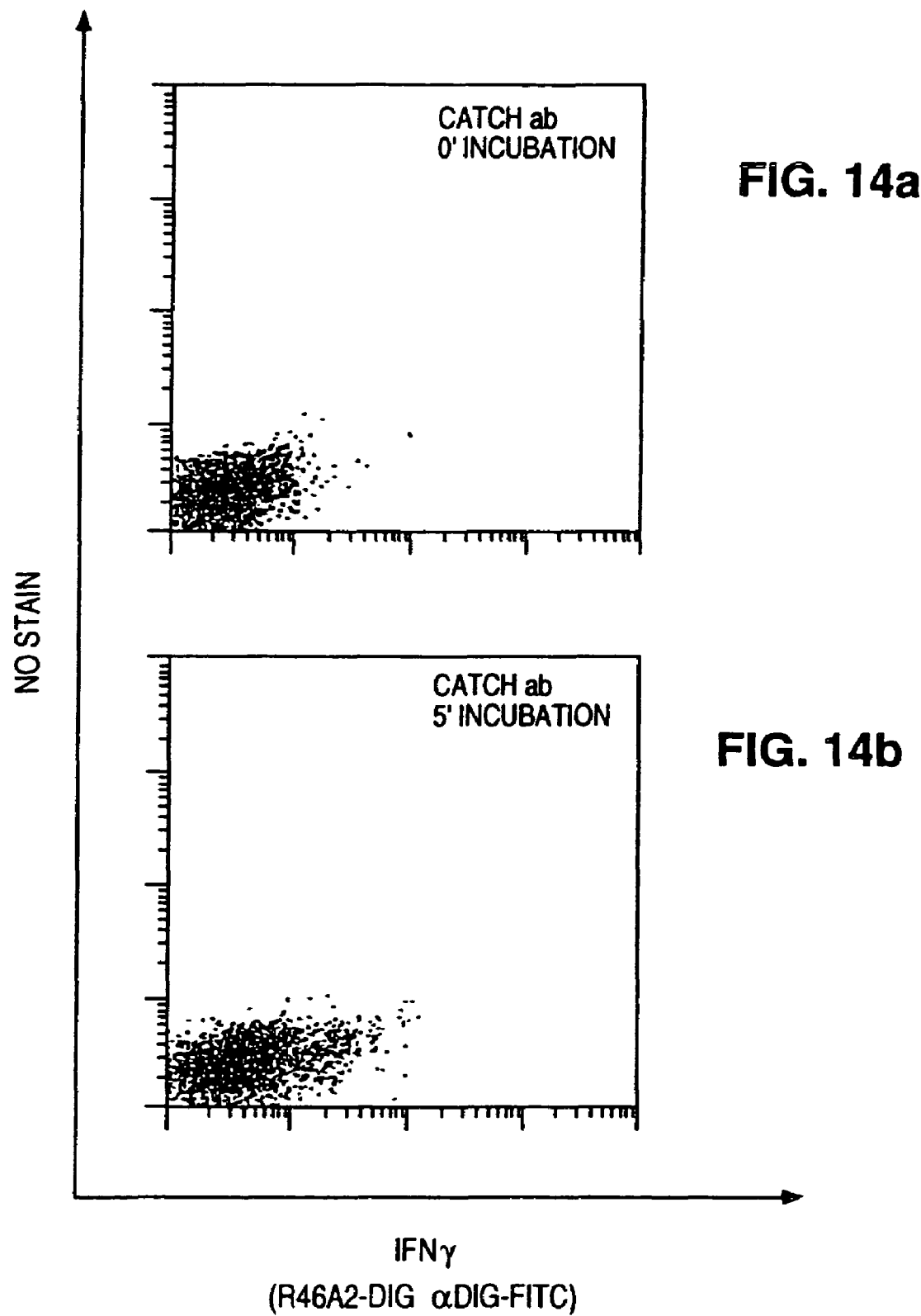
FIG. 14 is a compilation of dot plots of FACS analyses. In each instance, the abscissa represents the amount of label staining for interferon$\gamma$ (IFN$\gamma$) the ordinate represents no information. Cells were labeled with FITC labeled anti-digoxigenin antibody detecting digoxigenin-conjugated rat anti-mouse IFNγ antibody (R46A2-DIG αDIG-FITC). 14a is the result obtained at zero time incubation with catch antibody specific for IFNγ (catch ab). 14b is the result obtained with a 5 min incubation with the catch ab. 14c is the result obtained with a 90 min incubation without the catch ab. 14d is the result obtained with a 40 min incubation with the catch ab. 14e is the result obtained when the cells with catch ab are incubated in the presence of supernatant obtained from cells secreting IFN-γ (IFNγ sup). 14f is the result obtained with a 90 min incubation with catch ab.
Figures 14C, 14D:
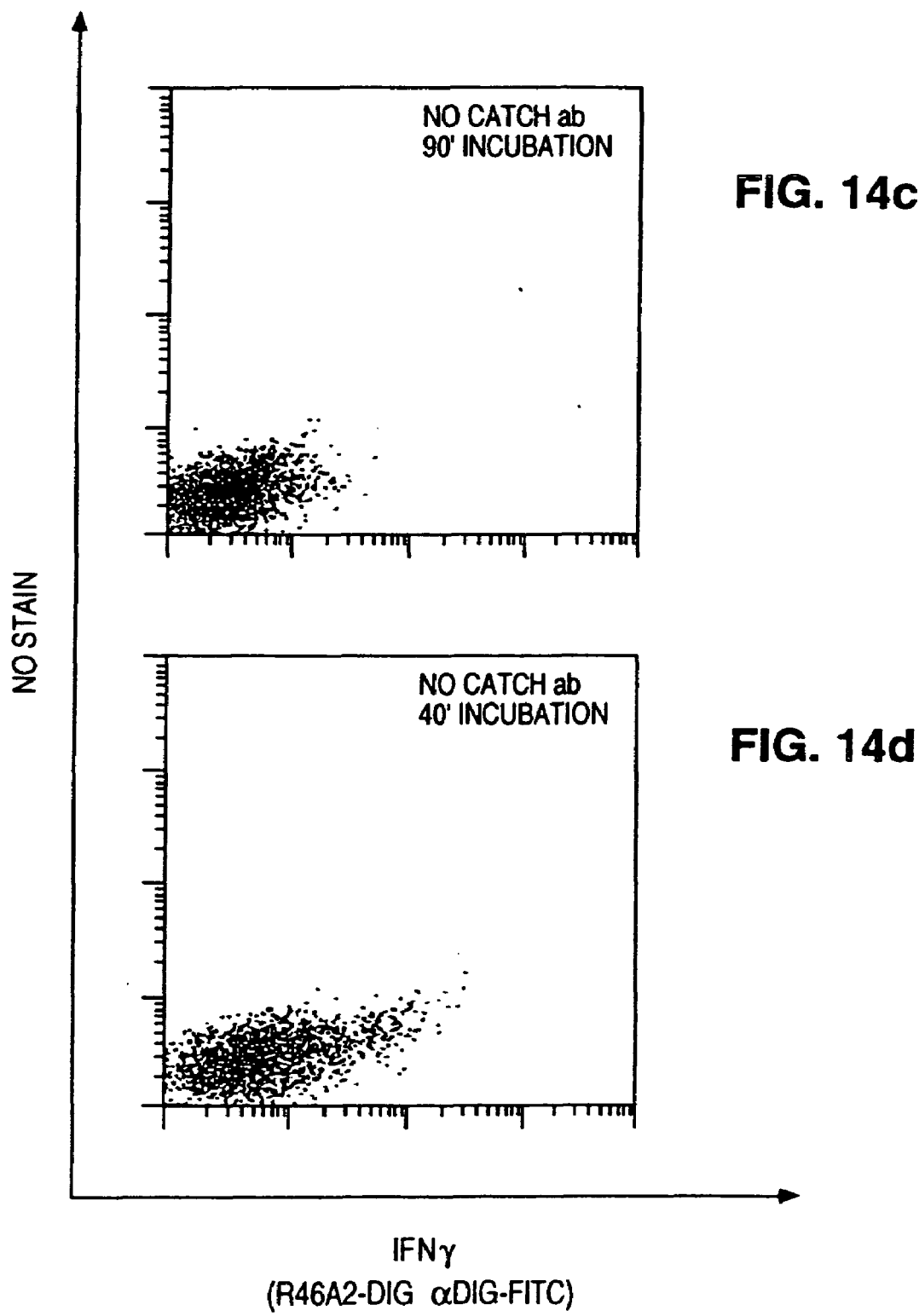

FIG. 14 depicts the number of cells labeled with αDIG-FITC under varying conditions. The αDIG-FITC binds to the anti-IFNγ antibody coupled to DIG R46A2-DIG. FIG. 14a depicts the number of cells labeled in the presence of catch-ab at zero time. FIGS. 14b, d and f depict the number of cells labeled in the presence of catch-ab after incubations of 5, 40 and 90 min. Note that some cells have already been labeled and increasingly more are labeled after 90 min. FIG. 14c depicts the number of cells labeled in the absence of catch-ab after a 90-min incubation. FIG. 14e depicts the number of cells labeled with αDIG-FITC in the presence of catch-ab and exogenous IFNγ added during the incubation.

INDUSTRIAL UTILITY

The above-described methods and compositions are useful for the detection and/or separation of cells that secrete varying levels of one or more designated substances. The cells may be phenotypically identical except for their secretory activity of the designated product. Thus, the method may be of use in separating cells that secrete commercially valuable substances from those that do not, for example, cells that secrete immunogenic polypeptides, growth factors, molecules that can act as hormones, and a variety of other products, including those produced by recombinant techniques. In addition, the techniques may be useful in the isolation of cell groups that are destined for transplantation or implantation procedures, or for packaging for implantation. Illustrative of this type of cell group are the islets of Langerhans, where it would be desirable to segregate groups of cells that are capable of secreting insulin from those that are non-secretors. The methods of determining the distribution of secretory activity of cells in cell mixtures are also of use in large scale fermentations in that they quickly identify the appearance of nonsecretory or low secretory cell variants or of cells producing a modified product.

The invention claimed is:

1. A method to positively identify cells based on a product secreted by the cells, comprising culturing said cells under conditions wherein the product is secreted and bound to a capture moiety coupled to said cells wherein said capture moiety specifically binds the product, thereby labeling cells with said product, and wherein said product is labeled with a label moiety, and wherein said cells are not lysed during said method.

2. A method to positively identify cells based on a product secreted by the cells, comprising the steps of:
   a) coupling said cells to a capture moiety;
   b) culturing said cells under conditions wherein the product is secreted and bound to said capture moiety, thereby labeling cells with a product secreted by said cells; and
   c) labeling said product with a label moiety, wherein said cells are not lysed during said method.

3. The method of claim 1 wherein said capture moiety is coupled to said cells through an anchoring moiety.

4. The method of claim 2 wherein said capture moiety is coupled to said cells through an anchoring moiety.

5. The method of claim 1 wherein the label moiety is an antibody specific for the product.

6. The method of claim 1 wherein the label moiety is fluorochromated.

7. The method of claim 1 wherein the label moiety is magnetizable.

8. The method of claim 7 wherein the label moiety comprises colloidal magnetic particles with a typical diameter of about 5 to 200 nm.

9. The method of claim 1 wherein the capture moiety is an antibody or an antigen-binding fragment thereof.

10. The method of claim 9 wherein the antibody or antigen binding fragment thereof is bispecific.

11. A method to positively identify cells based on a product secreted by the cells, comprising culturing said cells under conditions wherein the product is secreted and bound to a capture moiety coupled to said cells, wherein said capture moiety specifically binds the product, thereby labeling cells with said product, wherein said product is labeled with a label moiety, wherein said cells are not lysed during said method, wherein said capture moiety is coupled to said cells through an anchoring moiety, and wherein the anchoring moiety is a lipid anchor.

12. A method to positively identify cells based on a product secreted by the cells, comprising culturing said cells under conditions wherein the product is secreted and bound to a capture moiety coupled to said cells, wherein said capture moiety specifically binds the product, thereby labeling cells with said product, wherein said product is labeled with a label moiety, wherein said cells are not lysed during said method, wherein said capture moiety is coupled to said cells through an anchoring moiety, and wherein the anchoring moiety is an antibody, or an antigen-binding fragment thereof.

13. A method to positively identify cells based on a product secreted by the cells, comprising culturing said cells under conditions wherein the product is secreted and bound to a capture moiety coupled to said cells, wherein said capture moiety specifically binds the product, thereby labeling cells with said product, wherein said product is labeled with a label moiety, wherein said cells are not lysed during said method, and wherein said capture moiety is coupled to said cells through direct chemical coupling of the capture moiety to components on the cell surface, optionally through a linking moiety.

14. The method of claim 10 wherein the bispecific antibody specifically binds to the cell.

15. The method of claim 1 wherein said product is a cytokine, antibody, hormone or enzyme.

16. The method of claim 15 wherein the product is IFNγ, IL1, IL2, IL4, IL10, IL12, TGFβ, TNF, GMCSF, and SCF.

17. The method of claim 13 wherein said linking moiety comprises a branched polymer.

18. The method of claim 17 wherein said branched polymer comprises a modified dextran molecule, polyethylene glycol, polypropylene glycol, polyvinyl alcohol or polyvinylpyrrolidone.

19. The method of claim 1 wherein said cell comprises a cell surface marker.

20. The method of claim 19 wherein said cell surface marker includes CD3, CD4, CD8, CD19, CD20, CD14, CD16, CD15, CD45, class I MHC and Class II MHC molecules, CD34, CD38, CD33, CD56 T cell receptor, Fc receptor, β2 microglobulin or immunoglobulin.

21. The method of claim 19 wherein said cell surface marker comprises a cell adhesion molecule.

22. A composition comprising cells positively identified based on a product secreted by said cells, wherein said cells are coupled to a capture moiety, wherein said product secreted by said cells is bound to said capture moiety, and wherein said product is labeled with a label moiety, wherein said capture moiety is an antibody or antigen-binding fragment thereof.

23. The composition of claim 22 wherein said antibody is bispecific.

24. The composition of claim 22 wherein said capture moiety is coupled to said cells through an anchoring moiety and said anchoring moiety is an antibody or an antigen-binding fragment thereof.

25. A composition comprising cells positively identified based on a product secreted by said cells, wherein said cells are coupled to a capture moiety, wherein said product secreted by said cells is bound to said capture moiety, and wherein said product is labeled with a label moiety, wherein the label moiety is fluorochromated.

26. A composition comprising cells positively identified based on a cytokine secreted by said cells, wherein said cells are coupled to a capture moiety, wherein said cytokine secreted by said cells is bound to said capture moiety, and wherein said cytokine is labeled with a label moiety, and wherein said cytokine is IFNγ, IL1, IL2, IL4, IL10, IL12, TGFβ, TNF, GMCSF, and SCF.

27. A composition comprising cells positively identified based on a product secreted by said cells, wherein said cells are coupled to a capture moiety, wherein said product secreted by said cells is bound to said capture moiety, and wherein said product is labeled with a label moiety, wherein said capture moiety is coupled to said cells through direct chemical coupling of the capture moiety to components on the cell surface, optionally through a linking moiety wherein said linking moiety includes a branched polymer.

28. The composition of claim 27 wherein said branched polymer is a modified dextran molecules, polyethylene glycol, polypropylene glycol, polyvinyl alcohol or polyvinylpyrrolidone.

29. A method to positively identify cells based on a product secreted by the cells, comprising culturing said cells under conditions wherein the product is secreted and bound to a capture moiety coupled to said cells, wherein said capture moiety specifically binds the product, thereby labeling cells with said product, and wherein said product is labeled with a label moiety, wherein said cells are not lysed during said method further comprising the step of positively separating said cells labeled with said product.

30. A method to positively separate cells based on a product secreted by the cells, comprising the steps of:
 a) culturing cells coupled to a capture moiety under conditions wherein a product is secreted, wherein said product secreted by said cells specifically binds to said capture moiety, thereby producing cells labeled with said product, wherein said cells are not lysed by said method, and wherein said product is labeled with a label moiety; and
 b) positively separating said cells labeled with said product.

31. The method of claim 29 wherein said capture moiety is coupled to said cells through an anchoring moiety.

32. The method of claim 30 wherein said capture moiety is coupled to said cells through an anchoring moiety.

33. The method of claim 29 wherein the label moiety is an antibody specific for the product.

34. The method of claim 29 wherein the label moiety is fluorochromated.

35. The method of claim 29 wherein the label moiety is magnetizable.

36. The method of claim 35 wherein the label moiety comprises colloidal magnetic particles with a typical diameter of about 5 to 200 nm.

37. The method of claim 29 wherein the capture moiety is an antibody or an antigen-binding fragment thereof.

38. The method of claim 37 wherein the antibody or antigen binding fragment thereof is bispecific.

39. The method of claim 31 wherein the anchoring moiety is a lipid anchor.

40. The method of claim 31 wherein the anchoring moiety is an antibody, or an antigen-binding fragment thereof.

41. The method of claim 29 wherein said capture moiety is coupled to said cells through direct chemical coupling of the capture moiety to components on the cell surface, optionally through a linking moiety.

42. The method of claim 38 wherein the bispecific antibody specifically binds to the cell.

43. The method of claim 29 wherein said product is a cytokine, antibody, hormone or enzyme.

44. The method of claim 43 wherein said product is a cytokine.

45. The method of claim 43 wherein said product is an antibody.

46. The method of claim 44 wherein said cytokine is IFNγ, IL1, IL2, IL4, IL10, IL12, TGFβ, TNF, GMCSF, or SCF.

47. The method of claim 46 wherein said cytokine is IFNγ.

48. The method of claim 46 wherein said cytokine is IL2.

49. The method of claim 46 wherein said cytokine is IL4.

50. The method of claim 46 wherein said cytokine is IL10.

51. The method of claim 46 wherein said cytokine is IL12.

52. The method of claim 46 wherein said cytokine is TNF.

53. The method of claim 41 wherein said linking moiety includes branched polymers.

54. The method of claim 53 wherein said branched polymers includes modified dextran molecules, polyethylene glycol, polypropylene glycol, polyvinyl alcohol or polyvinylpyrrolidone.

55. The method of claim 29 wherein the capture moiety is bound to a cell surface marker.

56. The method of claim 55 wherein said cell surface marker is CD3, CD4, CD8, CD19, CD20, CD14, CD16, CD15, CD45, a class I MHC molecule, a Class II MHC molecule, CD34, CD38, CD33, CD56 T cell receptor, Fc receptor, β2 microglobulin or immunoglobulin.

57. The method of claim 55 wherein said surface marker is CD45.

58. The method of claim 55 wherein said cell surface marker comprises a cell adhesion molecule.

59. A method to determine the proportion of cells labeled with a product in a cell population, wherein the cells labeled with the product secrete said product, comprising the steps of:
 a) culturing a cell population, wherein said cells of said population are coupled to a capture moiety which specifically binds a product secreted by said cells, under conditions wherein the product is secreted and bound to said capture moiety;
 b) labeling the cells of step a) with at least one additional label moiety that does not label the product bound to said capture moiety; and
 c) comparing the proportion of cells comprising secreted product bound to said capture moiety to the proportion of cells labeled with said label moiety, thereby determining the proportion of cells in the population that secretes the product; and
 wherein said cells are not lysed by said method.

60. A method to determine the amount of cells labeled with a product in a population of cells, wherein the cells are labeled with the product secrete said product, comprising the steps of:
 a) culturing a cell population, wherein cells of said population are coupled to a capture moiety that specifically binds a product secreted by said cells, under conditions wherein the product is secreted and bound to said capture moiety thereby producing cells labeled with said product; and
 b) determining the amount of cells labeled with said product;
 wherein said cells are not lysed by said method.

61. The method of claim 60 further comprising the step of determining the amount and type of product produced per cell labeled with said product.

62. The method of claim 60 further comprising the steps of:
 c) labeling the cells with a second capture moiety which specifically binds a second protein;
 d) culturing said cells under conditions wherein a second product is secreted and bound to said second capture moiety thereby producing cells labeled with said second product; and
 e) determining the amount of cells labeled with said second product.

63. The method of claim 62 further comprising the step of determining the amount and type of each product produced per cell labeled with product.

64. A method to positively separate cells based on a product secreted by the cells comprising separating cells labeled with the product, wherein said cells have been coupled to a capture moiety that specifically binds a product secreted by said cells and wherein said cells have been cultured under conditions wherein the product is secreted and bound to said capture moiety, thereby producing cells labeled with said product, wherein said cells are not lysed by said method and wherein said product is labeled with a label moiety.

65. A method to positively separate cells based on a product secreted by the cells comprising separating cells labeled with the product, wherein said cells have been coupled to a capture moiety that specifically binds a product secreted by said cells and wherein said cells have been cultured under conditions wherein the product is secreted and bound to said capture moiety, thereby producing cells labeled with said product, wherein said cells are not lysed by said method, wherein said product is labeled with a label moiety, and wherein said capture moiety is coupled to said cells through an anchoring moiety.

66. The method of claim 64 wherein the label moiety is an antibody specific for the product.

67. The method of claim 64 wherein the label moiety is fluorochromated.

68. The method of claim 64 wherein the label moiety is magnetizable.

69. The method of claim 68 wherein the label moiety comprises colloidal magnetic particles with a typical diameter of about 5 to 200 nm.

70. The method of claim 64 wherein the capture moiety is an antibody or an antigen-binding fragment thereof.

71. The method of claim 70 wherein said antibody is against a cell surface antigen.

72. The method of claim 65 wherein the anchoring moiety is a lipid anchor.

73. The method of claim 65 wherein the anchoring moiety is an antibody, or an antigen-binding fragment thereof.

74. A method to positively separate cells based on a product secreted by the cells comprising separating cells labeled with the product, wherein said cells have been coupled to a capture moiety that specifically binds a product secreted by said cells and wherein said cells have been cultured under conditions wherein the product is secreted and bound to said capture moiety, thereby producing cells labeled with said product, wherein said cells are not lysed by said method, wherein said product is labeled with a label moiety, and wherein said capture moiety is coupled to said cells through direct chemical coupling of the capture moiety to components on the cell surface, optionally through a linking moiety.

75. The method of claim 64 wherein the product is a cytokine, antibody or hormone.

76. The method of claim 64 wherein said product is an antibody.

77. The method of claim 64 wherein said product is a cytokine.

78. The method of claim 77 wherein said cytokine is interleukin.

79. The method of claim 77 wherein said cytokine is IFNγ.

80. The method of claim 75 wherein said product is a growth hormone.

81. A method to determine the amount of product produced per cell in a population of cells, comprising the steps of:
  a) culturing a cell population, wherein said cells of said population are coupled to a capture moiety which specifically binds a product secreted by said cells, under conditions wherein the product is secreted and bound to said capture moiety thereby producing cells labeled with said product; and
  b) determining the amount of product produced per cell labeled with said product.

82. A method to label cells with a product secreted by the cells, comprising culturing said cells under conditions wherein the product is secreted and bound to a capture moiety coupled to said cells, wherein said capture moiety specifically binds the product, thereby labeling cells with said product, and wherein said product is optionally labeled with a label moiety, and wherein said cells are not lysed during said method.

83. The method of claim 82 wherein said capture moiety is coupled to said cells through an anchoring moiety.

84. The method of claim 82 wherein the capture moiety is an antibody or an antigen-binding fragment thereof.

85. The method of claim 82 wherein the antibody or antigen binding fragment thereof is bispecific.

86. A method to label cells with a product secreted by the cells, comprising culturing said cells under conditions wherein the product is secreted and bound to a capture moiety coupled to said cells, wherein said capture moiety specifically binds the product, thereby labeling cells with said product, wherein said product is optionally labeled with a label moiety, wherein said cells are not lysed during said method, wherein said capture moiety is coupled to said cells through an anchoring moiety, and wherein the anchoring moiety is a lipid anchor.

87. A method to label cells with a product secreted by the cells, comprising culturing said cells under conditions wherein the product is secreted and bound to a capture moiety coupled to said cells, wherein said capture moiety specifically binds the product, thereby labeling cells with said product, wherein said product is optionally labeled with a label moiety, wherein said cells are not lysed during said method, wherein said capture moiety is coupled to said cells through an anchoring moiety, and wherein the anchoring moiety is an antibody, or an antigen-binding fragment thereof.

88. A method to label cells with a product secreted by the cells, comprising culturing said cells under conditions wherein the product is secreted and bound to a capture moiety coupled to said cells, wherein said capture moiety specifically binds the product, thereby labeling cells with said product, wherein said product is optionally labeled with a label moiety, wherein said cells are not lysed during said method, and wherein said capture moiety is coupled to said cells through direct chemical coupling of the capture moiety to components on the cell surface, optionally through a linking moiety.

89. The method of claim 85 wherein the bispecific antibody specifically binds to the cell.

90. The method of claim 82 wherein said product is a cytokine antibody, hormone or enzyme.

91. The method of claim 90 wherein the product is IFNγ, IL1, IL2, IL4, IL10, IL12, TGFβ, TNF, GMCSF, and SCF.

92. The method of claim 88 wherein said linking moiety comprises a branched polymer.

93. The method of claim 92 wherein said branched polymer comprises a modified dextran molecule, polyethylene glycol, polypropylene glycol, polyvinyl alcohol or polyvinylpyrrolidone.

94. The method of claim 82 wherein said capture moiety is coupled to a cell surface marker.

95. The method of claim 94 wherein said cell surface marker is CD3, CD4, CD8, CD19, CD20, CD14, CD16, CD15, CD45, class I MHC and Class II MHC molecules, CD34, CD38, CD33, CD56 T cell receptor, Fc receptor, β2 microglobulin or immunoglobulin.

96. The method of claim 94 wherein said cell surface marker comprises a cell adhesion molecule.

97. A composition comprising cells labeled with a product secreted by said cells, wherein said cells are coupled to a capture moiety, wherein said product secreted by said cells is bound to said capture moiety, and wherein optionally, said product is labeled with a label moiety, wherein said capture moiety is an antibody or antigen-binding fragment thereof.

98. The composition of claim 97 wherein said antibody is bispecific.

99. A composition comprising cells labeled with a product secreted by said cells, wherein said cells are coupled to a capture moiety, wherein said product secreted by said cells is bound to said capture moiety, and wherein optionally, said product is labeled with a label moiety wherein said capture moiety is coupled to said cells through an anchoring moiety wherein said anchoring moiety is an antibody or an antigen-binding fragment thereof.

100. The composition according to claim 97 wherein the label moiety is fluorochromated.

101. The composition of claim 97 wherein said cytokine includes IFNγ, IL1, IL2, IL4, IL10, IL12, TGFβ, TNF, GMCSF, and SCF.

102. A The composition comprising cells labeled with a product secreted by said cells, wherein said cells are coupled to a capture moiety, wherein said product secreted by said cells is bound to said capture moiety, and wherein optionally, said product is labeled with a label moiety
wherein said capture moiety is coupled to said cells through direct chemical coupling of the capture moiety to components on the cell surface, optionally through a linking moiety wherein said linking moiety comprises a branched polymer.

103. The composition of claim 102 wherein said branched polymer comprises a modified dextran molecule, polyethylene glycol, polypropylene glycol, polyvinyl alcohol or polyvinylpyrrolidone.

104. The method of claim 62 further comprising the steps of, labeling the cells of claim 62 with at least one additional capture moiety which specifically binds an additional product; culturing said cells under conditions wherein said additional product is secreted and bound to said additional capture moiety thereby producing cells labeled with said additional product; and determining the amount of cells labeled with each product.

105. A method to determine the proportion of cells in a cell population that are labeled with a product, wherein the cells labeled with the product secrete the product, said method comprising:
a) culturing a cell population, wherein cells of said cell population are coupled to a capture moiety that specifically binds a product secreted by at least some cells in said cell population, under conditions wherein the product is secreted and bound to said capture moiety, thereby producing cells labeled with said product; and
b) determining the proportion of cells in said cell population that are labeled with said product; wherein said cells are not lysed by said method.

106. The method of claim 105, further comprising the steps of:
c) labeling the cells of said cell population with the second capture moiety that specifically binds a second product;
d) culturing said cell population under conditions wherein a second product is secreted and bound to said second capture moiety thereby producing cells labeled with said second product; and
e) determining the proportion of cells labeled with each product.

107. The method of claim 106 further comprising the step of determining the amount and type of each product produced per cell labeled with product.

108. A method to positively identify cells based on a product secreted by the cells, comprising culturing said cells under conditions wherein the product is secreted and bound to a capture moiety coupled to said cells wherein said capture moiety specifically binds the product, thereby labeling cells with said product, wherein said product is labeled with a label moiety, wherein said cells are not lysed during said method,
and wherein
a) said capture moiety is coupled to said cells through direct chemical coupling of the capture moiety to components on the cell surface, optionally through a linking moiety or
b) said capture moiety is coupled to said cells through an anchoring moiety, and
i) the anchoring moiety is a lipid anchor or
ii) the anchoring moiety is an antibody, or an antigen-binding fragment thereof.

109. A method to positively identify cells based on a product secreted by the cells, comprising culturing said cells under conditions wherein the product is secreted and bound to a capture moiety coupled to said cells wherein said capture moiety specifically binds the product, thereby labeling cells with said product, wherein said product is labeled with a label moiety, wherein said cells are not lysed during said method,
wherein said capture moiety is coupled to said cells through an anchoring moiety, and wherein the anchoring moiety is a lectin.

110. A method to positively identify cells based on a product secreted by the cells, comprising culturing said cells under conditions wherein the product is secreted and bound to a capture moiety coupled to said cells wherein said capture moiety specifically binds the product, thereby labeling cells with said product, wherein said product is labeled with a label moiety, wherein said cells are not lysed during said method,
wherein said capture moiety is an antibody or antigen binding fragment thereof, the antibody or antigen binding fragment thereof is bispecific, and the coupling is through specific binding of the antibody to the cell.

111. A method to positively identify cells based on a product secreted by the cells, comprising the steps of:
a) coupling said cells to a capture moiety;
b) culturing said cells under conditions wherein the product is secreted and bound to said capture moiety, thereby labeling cells with a product secreted by said cells; and
c) labeling said product with a label moiety, wherein said cells are not lysed during said method,
wherein
i) said capture moiety is coupled to said cells through direct chemical coupling of the capture moiety to components on the cell surface, optionally through a linking moiety or
ii) said capture moiety is coupled to said cells through an anchoring moiety, and
A) the anchoring moiety is a lipid anchor or
B) the anchoring moiety is an antibody, or an antigen-binding fragment thereof.

112. A method to positively identify cells based on a product secreted by the cells, comprising the steps of:
a) coupling said cells to a capture moiety;
b) culturing said cells under conditions wherein the product is secreted and bound to said capture moiety, thereby labeling cells with a product secreted by said cells; and
c) labeling said product with a label moiety, wherein said cells are not lysed during said method,
wherein said capture moiety is coupled to said cells through an anchoring moiety, and wherein the anchoring moiety is a lectin.

113. A method to positively identify cells based on a product secreted by the cells, comprising the steps of:
a) coupling said cells to a capture moiety;
b) culturing said cells under conditions wherein the product is secreted and bound to said capture moiety, thereby labeling cells with a product secreted by said cells; and
c) labeling said product with a label moiety, wherein said cells are not lysed during said method,
wherein said capture moiety is antibody or antigen binding fragment thereof, the antibody or antigen binding fragment thereof is bispecific, and the coupling is through specific binding of the antibody or antigen binding fragment thereof to the cell.

114. A method to positively separate cells based on a product secreted by the cells, comprising the steps of:

a) culturing cells coupled to a capture moiety under conditions wherein a product is secreted, wherein said product secreted by said cells specifically binds to said capture moiety, thereby producing cells labeled with said product wherein said cells are not lysed by said method, and wherein said product is labeled with a label moiety and wherein
   i) said capture moiety is coupled to said cells through direct chemical coupling of the capture moiety to components on the cell surface, optionally through a linking moiety or
   ii) said capture moiety is coupled to said cells through an anchoring moiety, and
      A) the anchoring moiety is a lipid anchor or
      B) the anchoring moiety is an antibody, or an antigen-binding fragment thereof; and
b) positively separating said cells labeled with said product.

115. A method to positively separate cells based on a product secreted by the cells, comprising the steps of:
   a) culturing cells coupled to a capture moiety under conditions wherein a product is secreted, wherein said product secreted by said cells specifically binds to said capture moiety, thereby producing cells labeled with said product wherein said cells are not lysed by said method, wherein said product is labeled with a label moiety, wherein said capture moiety is coupled to said cells through an anchoring moiety, and wherein the anchoring moiety is a lectin; and
   b) positively separating said cells labeled with said product.

116. A method to positively separate cells based on a product secreted by the cells, comprising the steps of:
   a) culturing cells coupled to a capture moiety under conditions wherein a product is secreted, wherein said product secreted by said cells specifically binds to said capture moiety, thereby producing cells labeled with said product wherein said cells are not lysed by said method, wherein said product is labeled with a label moiety, wherein said capture moiety is antibody or antigen binding fragment thereof, the antibody or antigen binding fragment thereof is bispecific, and the coupling is through specific binding of the antibody or antigen binding fragment thereof to the cell; and
   b) positively separating said cells labeled with said product.

117. A method to determine the proportion of cells labeled with a product in a cell population, wherein the cells labeled with the product secrete said product, comprising the steps of:
   a) culturing a cell population, wherein said cells of said population are coupled to a capture moiety which specifically binds a product secreted by said cells, under conditions wherein the product is secreted and bound to said capture moiety, wherein said product is labeled with a label moiety, and wherein
      i) said capture moiety is coupled to said cells through direct chemical coupling of the capture moiety to components on the cell surface, optionally through a linking moiety or
      ii) said capture moiety is coupled to said cells through an anchoring moiety, and
         A) the anchoring moiety is a lipid anchor or
         B) the anchoring moiety is an antibody, or an antigen-binding fragment thereof;
   b) labeling the cells of step a) with at least one additional label moiety that does not label the product bound to said capture moiety; and
   c) comparing the proportion of cells comprising secreted product bound to said capture moiety to the proportion of cells labeled with said label moiety, thereby determining the proportion of cells in the population that secretes the product; and
   wherein said cells are not lysed by said method.

118. A method to determine the proportion of cells labeled with a product in a cell population, wherein the cells labeled with the product secrete said product, comprising the steps of:
   a) culturing a cell population, wherein said cells of said population are coupled to a capture moiety which specifically binds a product secreted by said cells, under conditions wherein the product is secreted and bound to said capture moiety, wherein said capture moiety is coupled to said cells through an anchoring moiety, and wherein the anchoring moiety is a lectin;
   b) labeling the cells of step a) with at least one additional label moiety that does not label the product bound to said capture moiety; and
   c) comparing the proportion of cells comprising secreted product bound to said capture moiety to the proportion of cells labeled with said label moiety, thereby determining the proportion of cells in the population that secretes the product; and
   wherein said cells are not lysed by said method.

119. A method to determine the proportion of cells labeled with a product in a cell population, wherein the cells labeled with the product secrete said product, comprising the steps of:
   a) culturing a cell population, wherein said cells of said population are coupled to a capture moiety which specifically binds a product secreted by said cells, under conditions wherein the product is secreted and bound to said capture moiety, wherein said capture moiety wherein said capture moiety is antibody or antigen binding fragment thereof, the antibody or antigen binding fragment thereof is bispecific, and the coupling is through specific binding of the antibody or antigen binding fragment thereof to the cell;
   b) labeling the cells of step a) with at least one additional label moiety that does not label the product bound to said capture moiety; and
   c) comparing the proportion of cells comprising secreted product bound to said capture moiety to the proportion of cells labeled with said label moiety, thereby determining the proportion of cells in the population that secretes the product; and
   wherein said cells are not lysed by said method.

120. A method to determine the amount of cells labeled with a product in a population of cells, wherein the cells are labeled with the product secrete said product, comprising the steps of:
   a) culturing a cell population, wherein said cells of said population are coupled to a capture moiety which specifically binds a product secreted by said cells, under conditions wherein the product is secreted and bound to said capture moiety thereby producing cells labeled with said product, wherein
      i) said capture moiety is coupled to said cells through direct chemical coupling of the capture moiety to components on the cell surface, optionally through a linking moiety or ii) said capture moiety is coupled to said cells through an anchoring moiety, and
  A) the anchoring moiety is a lipid anchor or
  B) the anchoring moiety is an antibody, or an antigen-binding fragment thereof, and
b) determining the amount of cells labeled with said product; and
wherein said cells are not lysed by said method.

121. A method to determine the amount of cells labeled with a product in a population of cells, wherein the cells are labeled with the product secrete said product, comprising the steps of:
a) culturing a cell population, wherein said cells of said population are coupled to a capture moiety which specifically binds a product secreted by said cells, under conditions wherein the product is secreted and bound to said capture moiety thereby producing cells labeled with said product, wherein said capture moiety is coupled to said cells through an anchoring moiety, and wherein the anchoring moiety is a lectin; and
b) determining the amount of cells labeled with said product; and
wherein said cells are not lysed by said method.

122. A method to determine the amount of cells labeled with a product in a population of cells, wherein the cells are labeled with the product secrete said product, comprising the steps of:
a) culturing a cell population, wherein said cells of said population are coupled to a capture moiety which specifically binds a product secreted by said cells, under conditions wherein the product is secreted and bound to said capture moiety thereby producing cells labeled with said product, wherein said capture moiety is antibody or antigen binding fragment thereof, the antibody or antigen binding fragment thereof is bispecific, and the coupling is through specific binding of the antibody or antigen binding fragment thereof to the cell; and
b) determining the amount of cells labeled with said product; and
wherein said cells are not lysed by said method.

123. A method to positively separate cells based on a product secreted by the cells comprising separating cells labeled with the product, wherein said cells have been coupled to a capture moiety that specifically binds a product secreted by said cells, wherein said cells have been cultured under conditions wherein the product is secreted and bound to said capture moiety, thereby producing cells labeled with said product, wherein said cells are not lysed by said method, wherein said product is labeled with a label moiety, and wherein
i) said capture moiety is coupled to said cells through direct chemical coupling of the capture moiety to components on the cell surface, optionally through a linking moiety or
ii) said capture moiety is coupled to said cells through an anchoring moiety, and
  A) the anchoring moiety is a lipid anchor or
  B) the anchoring moiety is an antibody, or an antigen-binding fragment thereof.

124. A method to positively separate cells based on a product secreted by the cells comprising separating cells labeled with the product, wherein said cells have been coupled to a capture moiety that specifically binds a product secreted by said cells and wherein said cells have been cultured under conditions wherein the product is secreted and bound to said capture moiety, thereby producing cells labeled with said product, wherein said cells are not lysed by said method, wherein said product is labeled with a label moiety, wherein said capture moiety is coupled to said cells through an anchoring moiety, and wherein the anchoring moiety is a lectin.

125. A method to positively separate cells based on a product secreted by the cells comprising separating cells labeled with the product, wherein said cells have been coupled to a capture moiety that specifically binds a product secreted by said cells and wherein said cells have been cultured under conditions wherein the product is secreted and bound to said capture moiety, thereby producing cells labeled with said product, wherein said cells are not lysed by said method, wherein said product is labeled with a label moiety, wherein said capture moiety is an antibody or antigen binding fragment thereof, the antibody or antigen binding fragment thereof is bispecific, and the coupling is through specific binding of the antibody or antigen binding fragment thereof to the cell.

126. A method to determine the amount of product produced per cell in a population of cells, comprising the steps of:
a) culturing a cell population, wherein said cells of said population are coupled to a capture moiety which specifically binds a product secreted by said cells, under conditions wherein the product is secreted and bound to said capture moiety thereby producing cells labeled with said product, wherein said cells are not lysed by said method, wherein said product is labeled with a label moiety, and wherein
i) said capture moiety is coupled to said cells through direct chemical coupling of the capture moiety to components on the cell surface, optionally through a linking moiety or
ii) said capture moiety is coupled to said cells through an anchoring moiety, and
  A) the anchoring moiety is a lipid anchor or
  B) the anchoring moiety is an antibody, or an antigen-binding fragment thereof; and
b) determining the amount of product produced per cell labeled with said product.

127. A method to determine the amount of product produced per cell in a population of cells, comprising the steps of:
a) culturing a cell population, wherein said cells of said population are coupled to a capture moiety which specifically binds a product secreted by said cells, under conditions wherein the product is secreted and bound to said capture moiety thereby producing cells labeled with said product, wherein said capture moiety is coupled to said cells through an anchoring moiety, and wherein the anchoring moiety is a lectin; and
b) determining the amount of product produced per cell labeled with said product.

128. A method to determine the amount of product produced per cell in a population of cells, comprising the steps of:
a) culturing a cell population, wherein said cells of said population are coupled to a capture moiety which specifically binds a product secreted by said cells, under conditions wherein the product is secreted and bound to said capture moiety thereby producing cells labeled with said product, wherein said capture moiety is an antibody or antigen binding fragment thereof, the antibody or antigen binding fragment thereof is bispecific, and the coupling is through specific binding of the antibody or antigen binding fragment thereof to the cell; and b) determining the amount of product produced per cell labeled with said product.

129. A method to label cells with a product secreted by the cells, comprising culturing said cells under conditions wherein the product is secreted and bound to a capture moiety coupled to said cells, wherein said capture moiety specifically binds the product, thereby labeling cells with said product, and wherein said product is optionally labeled with a label moiety, wherein said cells are not lysed during said method, wherein said cells are not lysed by said method, wherein said product is labeled with a label moiety, and wherein i) said capture moiety is coupled to said cells through direct chemical coupling of the capture moiety to components on the cell surface, optionally through a linking moiety, or ii) said capture moiety is coupled to said cells through an anchoring moiety, and
 A) the anchoring moiety is a lipid anchor or
 B) the anchoring moiety is an antibody, or an antigen-binding fragment thereof.

130. A method to label cells with a product secreted by the cells, comprising culturing said cells under conditions wherein the product is secreted and bound to a capture moiety coupled to said cells, wherein said capture moiety specifically binds the product, thereby labeling cells with said product, and wherein said product is optionally labeled with a label moiety, wherein said cells are not lysed during said method, and wherein said capture moiety is coupled to said cells through an anchoring moiety, and wherein the anchoring moiety is a lectin.

131. A method to label cells with a product secreted by the cells, comprising culturing said cells under conditions wherein the product is secreted and bound to a capture moiety coupled to said cells, wherein said capture moiety specifically binds the product, thereby labeling cells with said product, and wherein said product is optionally labeled with a label moiety, wherein said cells are not lysed during said method, wherein said cells are not lysed by said method, wherein said product is labeled with a label moiety, and wherein said capture moiety is an antibody or antigen binding fragment thereof, the antibody or antigen binding fragment thereof is bispecific, and the coupling is through specific binding of the antibody or antigen binding fragment thereof to the cell.

132. The method of claim 3 wherein the anchoring moiety is a lipid anchor.

133. The method of claim 3 wherein the anchoring moiety is an antibody, or an antigen-binding fragment thereof.

134. The method of claim 4 wherein the anchoring moiety is a lipid anchor.

135. The method of claim 4 wherein the anchoring moiety is an antibody, or an antigen-binding fragment thereof.

136. The method of claim 32 wherein the anchoring moiety is a lipid anchor.

137. The method of claim 32 wherein the anchoring moiety is an antibody, or an antigen-binding fragment thereof.

138. The method of claim 83 wherein the anchoring moiety is a lipid anchor.

139. The method of claim 83 wherein the anchoring moiety is an antibody, or an antigen-binding fragment thereof.

140. The method of claim 59 wherein the capture moiety is an antibody or antigen binding fragment thereof.

141. The method of claim 140 wherein the antibody or antigen binding fragment thereof is bispecific, and the coupling is through specific binding of the antibody or antigen binding fragment thereof to the cell.

142. The method of claim 59 wherein said capture moiety is coupled to said cells through an anchoring moiety, wherein said anchoring moiety is a lipid anchor.

143. The method of claim 59 wherein said capture moiety is coupled to said cells through an anchoring moiety, and wherein the anchoring moiety is an antibody, or an antigen-binding fragment thereof.

144. The method of claim 60 wherein the capture moiety is an antibody or antigen binding fragment thereof.

145. The method of claim 144 wherein the antibody or antigen binding fragment thereof is bispecific, and the coupling is through specific binding of the antibody or antigen binding fragment thereof to the cell.

146. The method of claim 60 wherein said capture moiety is coupled to said cells through an anchoring moiety, and said anchoring moiety is a lipid anchor.

147. The method of claim 60 wherein said capture moiety is coupled to said cells through an anchoring moiety, and wherein said anchoring moiety is an antibody, or an antigen-binding fragment thereof.

148. The method of claim 71 wherein the antibody or antigen binding fragment thereof is bispecific, and the coupling is through specific binding of the antibody or antigen binding fragment thereof to the cell.

149. The method of claim 81 wherein the capture moiety is an antibody or antigen-binding fragment thereof.

150. The method of claim 149 wherein the antibody or antigen binding fragment thereof is bispecific, and the coupling is through specific binding of the antibody or antigen binding fragment thereof to the cell.

151. The method of claim 81 wherein said capture moiety is coupled to said cells through an anchoring moiety, and the anchoring moiety is a lipid anchor.

152. The method of claim 81 wherein said capture moiety is coupled to said cells through an anchoring moiety, and the anchoring moiety is an antibody, or an antigen-binding fragment thereof.

153. The method of claim 7 wherein label moiety is labeled either directly or indirectly with a fluorophore.

154. The method of claim 5 wherein label moiety is labeled either directly or indirectly with a magnetic particle.

155. The method of claim 2 wherein the label moiety is an antibody specific for the product.

156. The method of claim 155 wherein label moiety is labeled either directly or indirectly with a fluorophore.

157. The method of claim 155 wherein label moiety is labeled either directly or indirectly with a magnetic particle.

158. The method of claim 30 wherein the label moiety is an antibody specific for the product.

159. The method of claim 158 wherein label moiety is labeled either directly or indirectly with a fluorophore.

160. The method of claim 158 wherein label moiety is labeled either directly or indirectly with a magnetic particle.

161. The method of claim 59 wherein the label moiety is an antibody specific for the product.

162. The method of claim 161 wherein label moiety is labeled either directly or indirectly with a fluorophore.

163. The method of claim 161 wherein label moiety is labeled either directly or indirectly with a magnetic particle.

164. The method of claim 60 wherein the label moiety is an antibody specific for the product.

165. The method of claim 164 wherein label moiety is labeled either directly or indirectly with a fluorophore.

166. The method of claim 164 wherein label moiety is labeled either directly or indirectly with a magnetic particle.

167. The method of claim 64 wherein the label moiety is an antibody specific for the product.

168. The method of claim 167 wherein label moiety is labeled either directly or indirectly with a fluorophore.

169. The method of claim 167 wherein label moiety is labeled either directly or indirectly with a magnetic particle.

170. The method of claim 81 wherein the label moiety is an antibody specific for the product.

171. The method of claim 170 wherein label moiety is labeled either directly or indirectly with a fluorophore.

172. The method of claim 170 wherein label moiety is labeled either directly or indirectly with a magnetic particle.

173. The method of claim 108 wherein the label moiety is an antibody specific for the product.

174. The method of claim 173 wherein label moiety is labeled either directly or indirectly with a fluorophore.

175. The method of claim 173 wherein label moiety is labeled either directly or indirectly with a magnetic particle.

176. The method of claim 109 wherein the label moiety is an antibody specific for the product.

177. The method of claim 176 wherein label moiety is labeled either directly or indirectly with a fluorophore.

178. The method of claim 176 wherein label moiety is labeled either directly or indirectly with a magnetic particle.

179. The method of claim 110 wherein the label moiety is an antibody specific for the product.

180. The method of claim 179 wherein label moiety is labeled either directly or indirectly with a fluorophore.

181. The method of claim 179 wherein label moiety is labeled either directly or indirectly with a magnetic particle.

182. The method of claim 111 wherein the label moiety is an antibody specific for the product.

183. The method of claim 182 wherein label moiety is labeled either directly or indirectly with a fluorophore.

184. The method of claim 182 wherein label moiety is labeled either directly or indirectly with a magnetic particle.

185. The method of claim 112 wherein the label moiety is an antibody specific for the product.

186. The method of claim 185 wherein label moiety is labeled either directly or indirectly with a fluorophore.

187. The method of claim 185 wherein label moiety is labeled either directly or indirectly with a magnetic particle.

188. The method of claim 108 wherein the product is a cytokine.

189. The method of claim 109 wherein the product is a cytokine.

190. The method of claim 113 wherein the label moiety is an antibody specific for the product.

191. The method of claim 190 wherein label moiety is labeled either directly or indirectly with a fluorophore.

192. The method of claim 190 wherein label moiety is labeled either directly or indirectly with a magnetic particle.

193. The method of claim 114 wherein the label moiety is an antibody specific for the product.

194. The method of claim 193 wherein label moiety is labeled either directly or indirectly with a fluorophore.

195. The method of claim 193 wherein label moiety is labeled either directly or indirectly with a magnetic particle.

196. The method of claim 115 wherein the label moiety is an antibody specific for the product.

197. The method of claim 196 wherein label moiety is labeled either directly or indirectly with a fluorophore.

198. The method of claim 196 wherein label moiety is labeled either directly or indirectly with a magnetic particle.

199. The method of claim 116 wherein the label moiety is an antibody specific for the product.

200. The method of claim 199 wherein label moiety is labeled either directly or indirectly with a fluorophore.

201. The method of claim 199 wherein label moiety is labeled either directly or indirectly with a magnetic particle.

202. The method of claim 117 wherein the label moiety is an antibody specific for the product.

203. The method of claim 202 wherein label moiety is labeled either directly or indirectly with a fluorophore.

204. The method of claim 202 wherein label moiety is labeled either directly or indirectly with a magnetic particle.

205. The method of claim 118 wherein the label moiety is an antibody specific for the product.

206. The method of claim 205 wherein label moiety is labeled either directly or indirectly with a fluorophore.

207. The method of claim 205 wherein label moiety is labeled either directly or indirectly with a magnetic particle.

208. The method of claim 119 wherein the label moiety is an antibody specific for the product.

209. The method of claim 208 wherein label moiety is labeled either directly or indirectly with a fluorophore.

210. The method of claim 208 wherein label moiety is labeled either directly or indirectly with a magnetic particle.

211. The method of claim 120 wherein the label moiety is an antibody specific for the product.

212. The method of claim 211 wherein label moiety is labeled either directly or indirectly with a fluorophore.

213. The method of claim 211 wherein label moiety is labeled either directly or indirectly with a magnetic particle.

214. The method of claim 121 wherein the label moiety is an antibody specific for the product.

215. The method of claim 214 wherein label moiety is labeled either directly or indirectly with a fluorophore.

216. The method of claim 214 wherein label moiety is labeled either directly or indirectly with a magnetic particle.

217. The method of claim 122 wherein the label moiety is an antibody specific for the product.

218. The method of claim 217 wherein label moiety is labeled either directly or indirectly with a fluorophore.

219. The method of claim 217 wherein label moiety is labeled either directly or indirectly with a magnetic particle.

220. The method of claim 123 wherein the label moiety is an antibody specific for the product.

221. The method of claim 220 wherein label moiety is labeled either directly or indirectly with a fluorophore.

222. The method of claim 220 wherein label moiety is labeled either directly or indirectly with a magnetic particle.

223. The method of claim 217 wherein the label moiety is an antibody specific for the product.

224. The method of claim 223 wherein label moiety is labeled either directly or indirectly with a fluorophore.

225. The method of claim 223 wherein label moiety is labeled either directly or indirectly with a magnetic particle.

226. The method of claim 218 wherein the label moiety is an antibody specific for the product.

227. The method of claim 226 wherein label moiety is labeled either directly or indirectly with a fluorophore.

228. The method of claim 226 wherein label moiety is labeled either directly or indirectly with a magnetic particle.

229. The method of claim 219 wherein the label moiety is an antibody specific for the product.

230. The method of claim 229 wherein label moiety is labeled either directly or indirectly with a fluorophore.

231. The method of claim 229 wherein label moiety is labeled either directly or indirectly with a magnetic particle.

232. The method of claim 220 wherein the label moiety is an antibody specific for the product.

233. The method of claim 232 wherein label moiety is labeled either directly or indirectly with a fluorophore.

234. The method of claim 232 wherein label moiety is labeled either directly or indirectly with a magnetic particle.

235. The method of claim 221 wherein the label moiety is an antibody specific for the product.

236. The method of claim 235 wherein label moiety is labeled either directly or indirectly with a fluorophore.

237. The method of claim 235 wherein label moiety is labeled either directly or indirectly with a magnetic particle.

238. The method of claim 110 wherein the product is a cytokine.

239. The method of claim 173 wherein the product is a cytokine.

240. The method of claim 174 wherein the product is a cytokine.

241. The method of claim 129 wherein the label moiety is an antibody specific for the product.

242. The method of claim 241 wherein label moiety is labeled either directly or indirectly with a fluorophore.

243. The method of claim 241 wherein label moiety is labeled either directly or indirectly with a magnetic particle.

244. The method of claim 130 wherein the label moiety is an antibody specific for the product.

245. The method of claim 244 wherein label moiety is labeled either directly or indirectly with a fluorophore.

246. The method of claim 244 wherein label moiety is labeled either directly or indirectly with a magnetic particle.

247. The method of claim 132 wherein the label moiety is an antibody specific for the product.

248. The method of claim 247 wherein label moiety is labeled either directly or indirectly with a fluorophore.

249. The method of claim 247 wherein label moiety is labeled either directly or indirectly with a magnetic particle.

250. The method of claim 175 wherein the product is a cytokine.

251. The method of claim 179 wherein the product is a cytokine.

252. A composition comprising viable cells labeled with a product secreted by said cells, wherein said cells are coupled to a capture moiety, wherein said product secreted by said cells is bound to said capture moiety and wherein said product is labeled with a label moiety, wherein said capture moiety is:
 a) coupled to said cells through direct chemical coupling of the capture moiety to components on the cell surface, optionally through a linking moiety: or
 b) coupled to said cells through an anchoring moiety, and
  i) the anchoring moiety is a lipid anchor or
  ii) the anchoring moiety is an antibody, or an antigen-binding fragment thereof; or
 c) coupled to said cells through an anchoring moiety, and wherein the anchoring moiety is a lectin.

253. A composition comprising viable cells labeled with a product secreted by said cells,
 wherein said cells are coupled to a capture moiety, said product secreted by said cells is bound to said capture moiety, and
 said product is labeled with a label moiety wherein said capture moiety is an antibody or antigen binding fragment thereof, the antibody or antigen binding fragment thereof is bispecific, and the coupling is through specific binding of the antibody or antigen binding fragment thereof to the cell.

254. The composition of claim 252 wherein said capture moiety is an antibody or antigen-binding fragment thereof and the label moiety is an antibody or antibody fragment specific for the product.

255. A composition comprising viable cells, wherein said cells are coupled to a capture moiety, wherein a product secreted by said cells is specifically bound to said capture moiety, and wherein said product is labeled with a label moiety that permits the labeled cells to be positively selected based on the presence of said label moiety wherein said capture moiety is coupled to said cells through an anchoring moiety, and wherein the anchoring moiety is a lectin.

256. The composition of claim 255 wherein said capture moiety is an antibody or antigen-binding fragment thereof and the label moiety is an antibody or antibody fragment specific for the product.

257. The composition of claim 256 wherein the label moiety is an antibody specific for the product, and the label moiety is labeled either directly or indirectly with a fluorophore, radioactive isotope, chromophore or magnetic particles.

258. A composition comprising viable cells labeled with a cytokine secreted by said cells, wherein said cells are coupled to a capture moiety, wherein said cytokine secreted by said cells is bound to said capture moiety, and wherein said cytokine is labeled with a label moiety.

259. A composition comprising viable cells labeled with a cytokine secreted by said cells, wherein said cells are coupled to a capture moiety, wherein said cytokine secreted by said cells is bound to said capture moiety, and wherein said cytokine is labeled with a label moiety, and wherein said capture moiety is:
 a) coupled to said cells through direct chemical coupling of the capture moiety to components on the cell surface, optionally through a linking moiety or
 b) coupled to said cells through an anchoring moiety, and
  i) the anchoring moiety is a lipid anchor or
  ii) the anchoring moiety is an antibody, or an antigen-binding fragment thereof.

260. The composition of claim 252 wherein the product is a cytokine.

261. The composition of claim 253 wherein the product is a cytokine.

262. The composition of claim 254 wherein the product is a cytokine.

263. A composition comprising viable cells, wherein said cells are coupled to a capture moiety, wherein a cytokine secreted by said cells is specifically bound to said capture moiety, and wherein said cytokine is labeled with a label moiety that permits the labeled cells to be positively selected based on the presence of said label moiety.

264. A composition comprising viable cells, wherein said cells are coupled to a capture moiety, wherein a cytokine secreted by said cells is specifically bound to said capture moiety, and wherein said cytokine is labeled with a label moiety that permits the labeled cells to be positively selected based on the presence of said label moiety wherein said capture moiety is:
 a) coupled to said cells through direct chemical coupling of the capture moiety to components on the cell surface, optionally through a linking moiety or b) coupled to said cells through an anchoring moiety, and
  i) the anchoring moiety is a lipid anchor or
  ii) the anchoring moiety is an antibody, or an antigen-binding fragment thereof.

265. The composition of claim 256 wherein the product is a cytokine.

266. The composition of claim 257 wherein the product is a cytokine.

267. The method of claim 82 wherein said product is labeled with a label moiety.

268. The method of claim 82 wherein said product is a protein.

269. The method of claim 1 wherein said product is a protein.

270. The method of claim 29 wherein said product is a protein.

271. The method of claim 64 wherein said product is a protein.

272. The method of claim 267 wherein the label moiety is an antibody specific for the product.

273. The method of claim 267 wherein the label moiety is fluorochromated.

274. The method of claim 267 wherein the label moiety is magnetizable.

275. The method of claim 274 wherein the label moiety comprises colloidal magnetic particles with a typical diameter of about 5 to 200 nm.

276. The method of claim 267 wherein the label moiety is an antibody specific for the product.

277. The method of claim 276 wherein the label moiety is labeled either directly or indirectly with a fluorophore.

278. The method of claim 276 wherein label moiety is labeled either directly or indirectly with a magnetic particle 279. The composition of claim 263 wherein said capture moiety is an antibody or antigen-binding fragment thereof and the label moiety is an antibody or antibody fragment specific for the product.

280. The composition of claim 264 wherein said capture moiety is an antibody or antigen-binding fragment thereof and the label moiety is an antibody or antibody fragment specific for the product.

281. The composition of claim 263 wherein said capture moiety is an antibody or antigen binding fragment thereof, the antibody or antigen binding fragment thereof, the antibody or antigen binding fragment thereof is bispecific, and the coupling is through specific binding of the antibody or antigen binding fragment thereof to the cell.

282. The composition of claim 279 wherein the label moiety is an antibody specific for the product, and the label moiety is labeled either directly or indirectly with a fluorophore, radioactive isotope, chromophore or magnetic particles.

283. The composition of claim 280 wherein the label moiety is an antibody specific for the product, and the label moiety is labeled either directly or indirectly with a fluorophore, radioactive isotope, chromophore or magnetic particles.

284. The composition of claim 279 wherein the product is a cytokine.

285. The composition of claim 255 wherein the product is a cytokine.

286. The composition of claim 280 wherein the product is a cytokine.

287. The composition of claim 281 wherein the product is a cytokine.

288. The composition of claim 282 wherein the product is a cytokine.

289. The composition of claim 283 wherein the product is a cytokine.

* * * * *